(12) United States Patent
Abe

(10) Patent No.: US 9,131,890 B2
(45) Date of Patent: Sep. 15, 2015

(54) INFORMATION PROCESSING APPARATUS, INFORMATION PROCESSING METHOD, PROGRAM, AND RECORDING MEDIUM

(75) Inventor: Makoto Abe, Tokyo (JP)

(73) Assignee: SonyCorporation, Tokyo (JP)

( * ) Notice: Subject to any disclaimer, the term of this patent is extended or adjusted under 35 U.S.C. 154(b) by 479 days.

(21) Appl. No.: 13/551,868

(22) Filed: Jul. 18, 2012

(65) Prior Publication Data

US 2013/0038459 A1    Feb. 14, 2013

(30) Foreign Application Priority Data

Aug. 10, 2011   (JP) ................................ 2011-175008

(51) Int. Cl.
*G08B 21/00* (2006.01)
*A61B 5/00* (2006.01)
*A61B 5/11* (2006.01)
*G06F 19/00* (2011.01)

(52) U.S. Cl.
CPC ................. *A61B 5/48* (2013.01); *A61B 5/1112* (2013.01); *A61B 5/6898* (2013.01); *A61B 5/7275* (2013.01); *G06F 19/3481* (2013.01)

(58) Field of Classification Search
CPC ...... A61B 5/1112; A61B 5/48; A61B 5/6898; A61B 5/7275; G06F 19/3481
USPC ...................... 340/686.1, 500, 540, 3.7–3.71, 340/5.3–5.33, 6.1–8.1; 600/300, 301
See application file for complete search history.

(56) References Cited

U.S. PATENT DOCUMENTS

2010/0063365 A1*   3/2010   Pisani et al. ................... 600/301

FOREIGN PATENT DOCUMENTS

| JP | 2002-22479 | 1/2002 |
|---|---|---|
| JP | 2007-20971 | 2/2007 |

* cited by examiner

*Primary Examiner* — Steven Lim
*Assistant Examiner* — Sisay Yacob
(74) *Attorney, Agent, or Firm* — Sony Corporation

(57) ABSTRACT

There is provided an information processing apparatus including an altitude information acquisition section which acquires altitude information, and a determination section which determines a degree of risk of physical strain on a user based on the altitude information.

17 Claims, 14 Drawing Sheets

FIG. 7

| WARNING MESSAGE 1 | You are at high altitude point.<br>Symptoms of altitude sickness may appear. Be careful. |
|---|---|
| WARNING MESSAGE 2 | Rapid altitude rise.<br>Symptoms of altitude sickness may appear. Be careful. |
| WARNING MESSAGE 3 | Altitude is high. Symptoms of altitude sickness may appear.<br>You are recommended to take a break. |

ALTITUDE CHANGE OF PLANNED ROUTE

ALTITUDE CHANGE OF PLANNED ROUTE

INFORMATION PROCESSING APPARATUS, INFORMATION PROCESSING METHOD, PROGRAM, AND RECORDING MEDIUM

BACKGROUND

The present disclosure relates to an information processing apparatus, an information processing method, a program, and a recording medium.

In recent years, the number of mountain climbers has been increasing. In order to safely climb a mountain, the management of physical condition takes an important role. In particular, the air is thin in high mountains compared to the air on the ground. Accordingly, blood oxygen content may decrease and a person may get altitude sickness that causes abnormalities in the person's body.

In order to assist the management of physical condition on the occasion of climbing a mountain, JP 2007-20971A suggests a device which determines the physical condition of a user and performs warning, based on biological data (for example, body temperature, blood pressure, and heart rate) of the user acquired by a biological sensor and meteorological data (for example, temperature, humidity, and atmospheric pressure) around the user, for example. Further, the JP 2002-22479A suggests a base station which determines the physical condition of a user based on the biological data of the user acquired by a biological sensor.

SUMMARY

However, the devices disclosed in JP 2007-20971A and JP 2002-22479A each use the biological data acquired by the biological sensor. Accordingly, it was troublesome for the user to attach the biological sensor to the body, and this was an obstacle to introduction of a physical condition management system.

In light of the foregoing, it is desirable to provide an information processing apparatus, an information processing method, a program, and a recording medium which are novel and improved, and which can determine the physical condition of the user on the occasion of climbing a mountain based on altitude.

According to an embodiment of the present disclosure, there is provided an information processing apparatus which includes an altitude information acquisition section which acquires altitude information, and a determination section which determines a degree of risk of physical strain on a user based on the altitude information.

According to such a configuration, a degree of risk of physical strain on the user (for example, a degree of risk that symptoms of altitude sickness may appear) can be determined based on the altitude information. The altitude information can be acquired without attaching a sensor to a specific part of the user's body. Accordingly, the degree of risk of physical strain on the user can be determined with a simple configuration compared to the case of using the biological sensor or the like.

According to another embodiment of the present disclosure, there is provided an information processing method which includes acquiring altitude information, and determining a degree of risk of physical strain on a user based on the altitude information.

According to another embodiment of the present disclosure, there is provided a program for causing a computer to function as an information processing apparatus including an altitude information acquisition section which acquires altitude information, and a determination section which determines a degree of risk of physical strain on a user based on the altitude information.

According to another embodiment of the present disclosure, there is provided a computer-readable recording medium having a program recorded therein, the program being for causing a computer to function as an information processing apparatus including an altitude information acquisition section which acquires altitude information, and a determination section which determines a degree of risk of physical strain on a user based on the altitude information.

According to the embodiments of the present disclosure described above, the physical condition of the user on the occasion of climbing a mountain can be determined based on altitude.

BRIEF DESCRIPTION OF THE DRAWINGS

FIG. 7 is a table showing an example of warning messages output by the PND according to the embodiment;

DETAILED DESCRIPTION OF THE EMBODIMENT(S)

Figure 1:
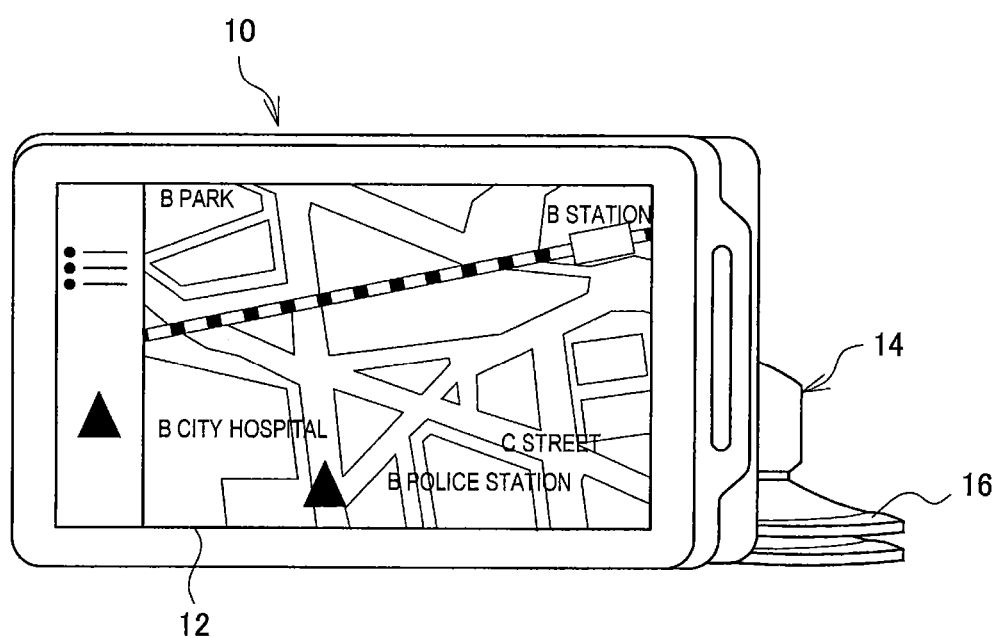
FIG. 1 is an external view of a PND according to a first embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that the description will be given in the following order.

1. Outline
2. First embodiment (Case of PND)
2-1. Configuration
2-2. Operation example
2-3. Calculation of rate of increase in altitude
2-4. Calculation of average travel speed
2-5. Calculation of estimated rate of increase in altitude
2-6. Division into intervals for calculation
3. Second embodiment (Case of determining degree of risk on server side)
3-1. Configuration
3-2. Operation
4. Third embodiment (Case of notification system)
4-1. Configuration
4-2. Operation

1. Outline

The present disclosure describes an information processing apparatus which determines a degree of risk of physical strain on the user based on altitude information. The physical strain on the user causes symptoms of altitude sickness. In particular, not only some mountain climbing enthusiasts but also more beginners have readily enjoyed mountain climbing recently. Accordingly, there are more occasions for the beginners to climb mountains. In climbing mountains, there are some points to which attention should be paid, which are different from those of the case of the ordinary life. Nevertheless, there are more occasions for the beginners to climb mountains, who do not have sufficient knowledge of the mountains.

In most cases, the mountain climbing enthusiast does not feel it troublesome to attach a biological sensor to his/her body to use it for the physical condition management, in order to more accurately know his/her physical condition. However, it is considered that most beginners feel it troublesome to attach a dedicated sensor for infrequent mountain climbing. Accordingly, there is a latent demand for a method capable of acquiring more simply information to be a standard for the user's physical condition management. Accordingly, there will be described an information processing apparatus which determines simply the degree of risk that symptoms of altitude sickness may appear.

The symptom of altitude sickness is likely to appear at places of high altitude. A main cause for the altitude sickness is deficiency in blood oxygen content. With the amount of oxygen consumed by physical exercise continuously exceeding the amount of oxygen supplied by respiration, the blood oxygen content decreases. It is highly likely that a symptom of the altitude sickness is avoided by suppressing the decrease in the blood oxygen content. In order to suppress the decrease in the blood oxygen content, oxygen may be supplied, the amount of which is greater than the amount of oxygen consumed by physical exercise. Accordingly, the possibility that the altitude sickness can be avoided is increased, only by paying attention to the way of climbing, for example, taking a rest and climbing slowly.

In particular, at mountains that are over 2400 meters high, it is said that symptoms of altitude sickness are likely to appear. Further, also in the case where the altitude is 2000 meters or higher, attention is necessary. With the increase in altitude, the oxygen content of the air decreases. Accordingly, it is effective to call the user's attention based on the altitude. Further, the rate of increase in altitude also relates to an incidence rate of altitude sickness. Accordingly, it is also effective to call the user's attention based on the rate of increase in altitude.

Hereinafter, first, there will be described as a first embodiment an example of application of an information processing apparatus, which determines the degree of risk that symptoms of altitude sickness may appear, to a PND (Personal Navigation Device). Further, there will be described as a second embodiment a server device, which determines the degree of risk that symptoms of altitude sickness may appear on a user of a mobile terminal. In addition, there will be described as a third embodiment a notification system, which determines the degree of risk and performs notification not only to the user himself/herself but also to an outside of the determination on the degree of risk.

2. First Embodiment

Case of PND

[2-1. Configuration]

Figure 2:
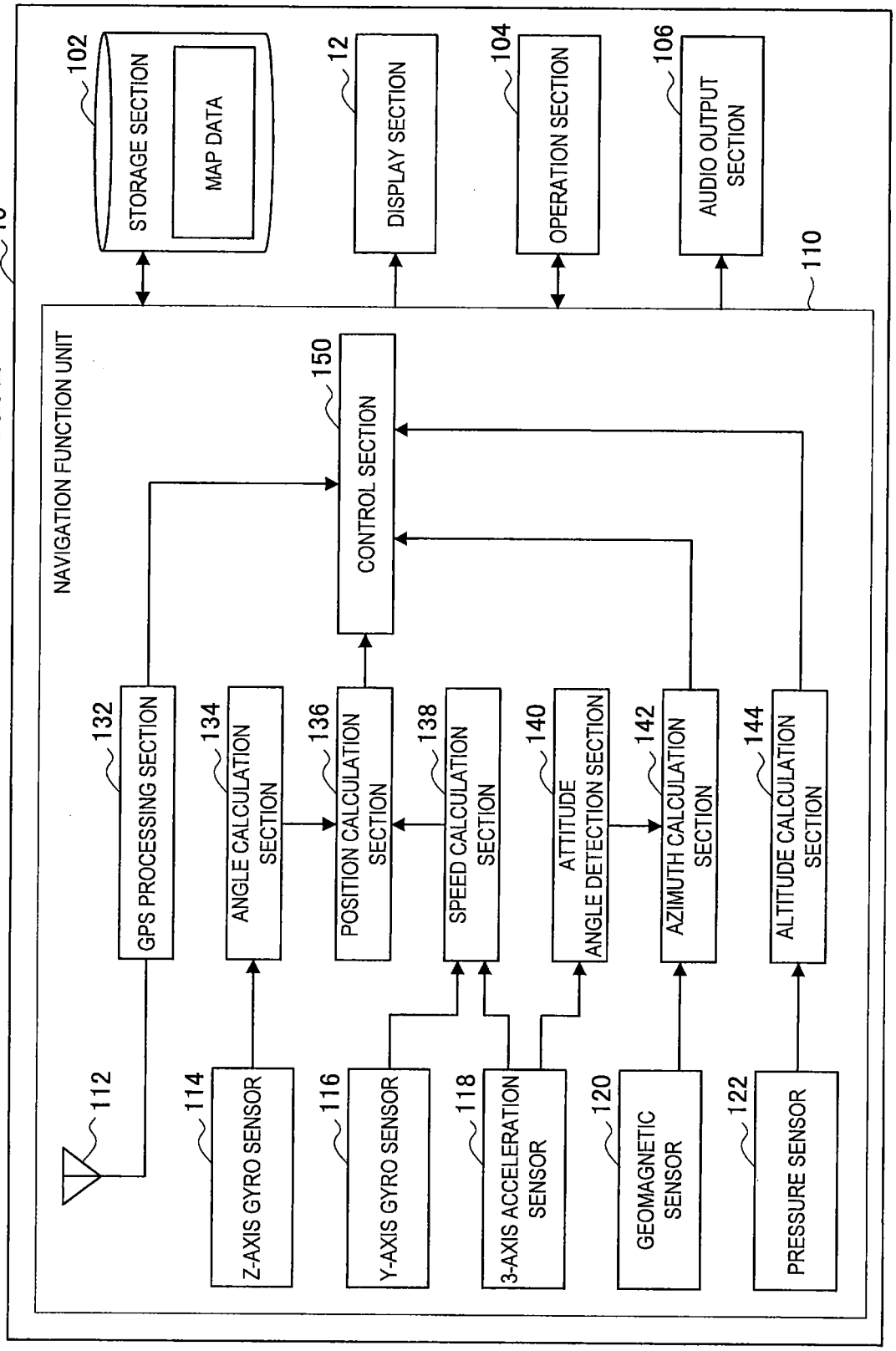
FIG. 2 is a block diagram showing a configuration of the PND according to the embodiment.
Figure 3:
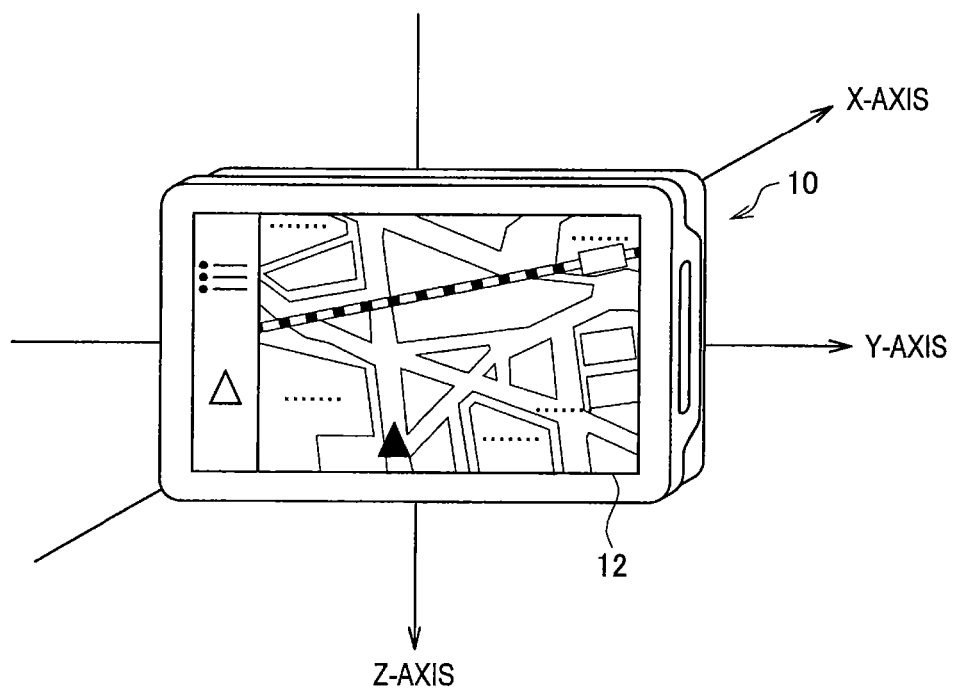
FIG. 3 is an explanatory diagram showing a coordinate system of the PND according to the embodiment.
Figure 4:
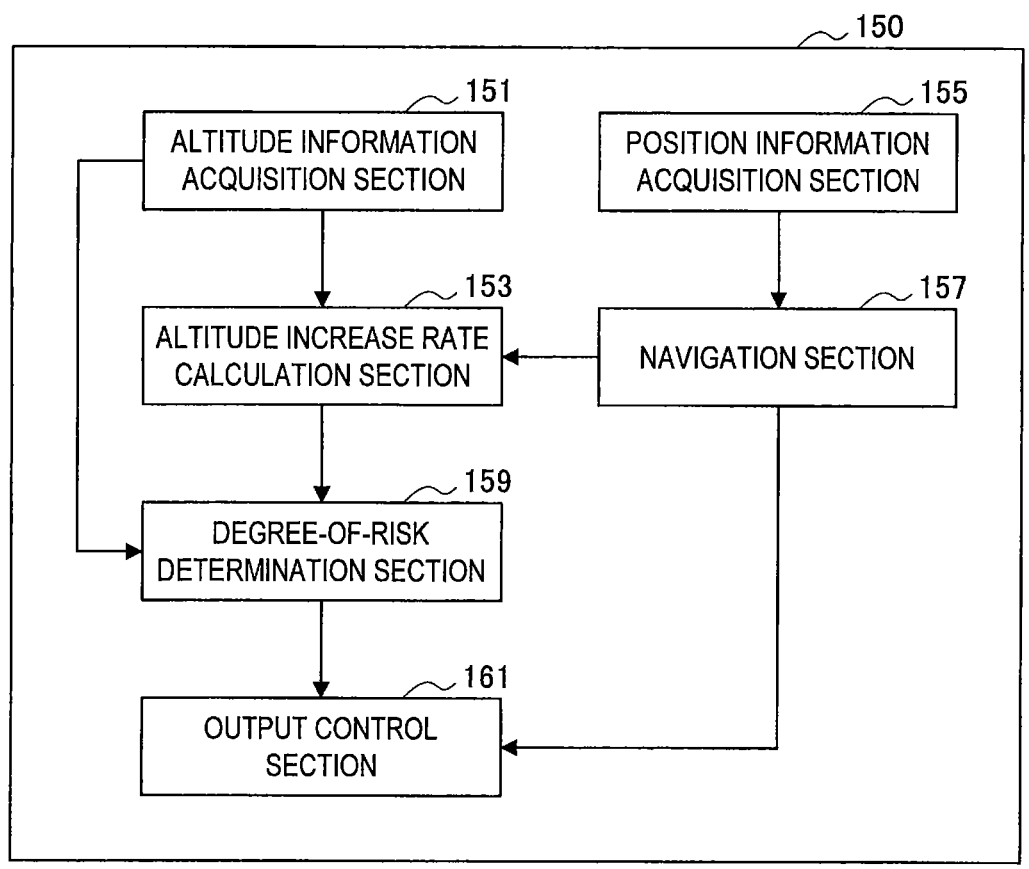
FIG. 4 is a block diagram showing a detailed configuration of a control section of the PND according to the embodiment.

Here, with reference to FIGS. 1 to 4, a configuration of a PND according to a first embodiment of the present disclosure will be described. FIG. 1 is an external view of the PND according to the first embodiment of the present disclosure. FIG. 2 is a block diagram showing a configuration of the PND according to the embodiment. FIG. 3 is an explanatory diagram showing a coordinate system of the PND according to the embodiment. FIG. 4 is a block diagram showing a detailed configuration of a control section of the PND according to the embodiment.

First, referring to FIG. 1, there is shown an appearance example of a PND (Personal Navigation Device) 10 serving as an example of an information processing apparatus which determines a degree of risk of physical strain on the user based on altitude information.

((PND 10))

The PND 10 has a navigation function of showing a route to a destination, and a function of providing a user with various pieces of information each associated with position information. The PND 10 has a display section 12 which displays an information providing screen on the front surface thereof that provides the user with various pieces of information, and the casing thereof is held by a cradle 14 for a vehicle which is attached to a dashboard of a vehicle via a suction cup 16. The PND 10 can be easily attached to and also detached from the cradle 14 for a vehicle. Accordingly, one PND 10 can be used on multiple vehicles. Further, the PND 10 may also be attached to a bicycle via a cradle for a bicycle.

Further, the PND 10 has a function of acquiring current position information of the PND 10, and also stores map data. Accordingly, the PND 10 can cause the display section 12 to display the current position information in a superimposed manner on a map. In addition, the PND 10 may record travel history information and may function as so-called GPS (Global Positioning System) logger. When functioning as the GPS logger, the PND 10 may reduce the power consumption by not causing the display section 12 to display the display screen.

Next, with reference to FIG. 2, an example of the configuration of the PND 10 will be described. The PND 10 mainly includes the display section 12, a storage section 102, an operation section 104, an audio output section 106, and a navigation function unit 110.

(Navigation Function Unit 110)

The navigation function unit 110 mainly includes a GPS antenna 112, a Z-axis gyro sensor 114, a Y-axis gyro sensor 116, a 3-axis acceleration sensor 118, a geomagnetic sensor 120, a pressure sensor 122, a GPS processing section 132, an angle calculation section 134, a position calculation section 136, a speed calculation section 138, an attitude angle detection section 140, an azimuth calculation section 142, an altitude calculation section 144, and a control section 150.

(Display Section 12)

The display section 12 is a display device which outputs a display screen to the user. For example, the display screen to be output may be a screen in which an icon or the like indicating a current position is superimposed on map data. The display section 12 may be a display device such as an LCD (Liquid Crystal Display) or an organic EL (Electroluminescence) display.

(Storage Section 102)

The storage section 102 is a storage medium which stores a program, map data, and the like for the PND 10 to operate. The storage section 102 may be, for example, a storage medium such as a non-volatile memory such as a Flash ROM (or Flash Memory), an EEPROM (Electrically Erasable Programmable Read-Only Memory), and an EPROM (Erasable Programmable ROM), a magnetic disk such as a hard disk and a disc-like magnetic disk, an optical disc such as a CD (Compact Disc), a DVD-R (Digital Versatile Disc Recordable), and a BD (Blu-Ray Disc (registered trademark)), and an MO (Magneto Optical) disk. Further, the map data stored in the storage section 102 may be stored in the storage section 102 in advance, at the time of shipping the PND 10. Further, the map data stored in the storage section 102 may be acquired via a communication section or a removable medium (not shown). Note that the map data may include altitude information of each point.

(Operation Section 104)

The operation section 104 accepts an operation instruction from the user, and outputs the operation contents to the navigation function unit 110. Examples of the operation instruction input by the user include setting a destination, enlarging/reducing the scale of a map, setting a vocal guidance, and setting a screen display. The operation section 104 may be a touch sensor which is provided in an integrated manner with the display section 12. Alternatively, the operation section 104 may have a physical configuration such as a button, a switch, or a lever, which is provided separately from the display section 12. Further, the operation section 104 may be a signal reception section which detects a signal indicating an operation instruction input by the user transmitted from a remote controller.

(Audio Output Section 106)

The audio output section 106 is an output device which outputs audio data, and may be a speaker. The audio output section 106 outputs navigation audio guidance of a travelling traffic lane and a turn direction while the navigation function unit is showing a route to a destination, for example. The user listens to the audio guidance, which enables the user to find out the route to take even without watching the display section 12. Further, the audio output section 106 can also perform audio output of a warning message when it is determined by degree-of-risk determination processing, which will be described later, that a degree of risk of physical strain on the user is high (there is a risk that the symptoms of altitude sickness may appear).

(GPS Antenna 112)

The GPS antenna 112 is capable of receiving GPS signals from multiple GPS satellites. The GPS antenna 112 inputs the received GPS signals to the GPS processing section 132. Note that the GPS signals received here may include orbital data indicating orbits of the GPS satellites and information such as transmission time of the signals.

(GPS Processing Section 132)

The GPS processing section 132 calculates position information indicating the current position of the PND 10 based on the multiple GPS signals input from the GPS antenna 112. The GPS processing section 132 supplies the control section 150 with the calculated position information. Specifically, the GPS processing section 132 can calculate a position of each of the GPS satellites from the orbital data obtained by demodulating each of the multiple GPS signals, and can calculate a distance between each of the GPS satellites and the PND 10 from a difference between a transmission time and a reception time of the GPS signal. Then, the GPS processing section 132 can calculate a current three-dimensional position based on the calculated positions of the respective GPS satellites and the distances from the respective GPS satellites to the PND 10.

In addition to the absolute position-acquisition function using the GPS antenna 112 and the GPS processing section 132, the navigation function unit 110 has a relative position-acquisition function using various sensors. Information of the relative position may be used in a situation where it is difficult for the PND 10 to acquire an absolute position, for example, in a situation where the PND 10 is at a position at which it is difficult to receive a GPS signal, such as inside a tunnel and a wood, where the skies are covered. Alternatively, the information of the relative position may be used in combination with the information of the absolute position.

(Z-Axis Gyro Sensor 114)

The Z-axis gyro sensor 114 is a sensor having a function of detecting, as a voltage value, a yaw rate $\omega_z$ which is a variable velocity (angular velocity) of the rotation angle around the Z-axis when the PND 10 is rotated. The Z-axis gyro sensor 114 detects the yaw rate $\omega_z$ at a predetermined sampling frequency, and inputs data indicating the detected yaw rate $\omega_z$ to the angle calculation section 134. Note that, as shown in FIG. 3, the Z-axis corresponds to the vertical direction. The X-axis corresponds to a travelling direction of the PND 10, and the Y-axis corresponds to the horizontal direction that is perpendicular to the X-axis.

(Angle Calculation Section 134)

The angle calculation section 134 calculates an angle θ of when the PND 10 is rotated by multiplying the yaw rate $\omega_z$ input from the Z-axis gyro sensor 114 by a sampling frequency, and inputs angle data indicating the angle θ to the position calculation section 136.

(Y-Axis Gyro Sensor 116)

The Y-axis gyro sensor 116 is a sensor having a function of detecting, as a voltage value, a pitch rate $\omega_y$ which is an angular velocity around the Y-axis. The Y-axis gyro sensor 116 detects the pitch rate $\omega_y$ at a predetermined sampling frequency, and inputs data indicating the detected pitch rate $\omega_y$ to the speed calculation section 138.

(3-Axis Acceleration Sensor 118)

The 3-axis acceleration sensor 118 is a sensor having a function of detecting, as voltage values, an acceleration $\alpha_x$ along the X-axis, an acceleration $\alpha_y$ along the Y-axis, and an acceleration $\alpha_z$ along the Z-axis. The 3-axis acceleration sensor 118 detects the acceleration $\alpha_x$, the acceleration $\alpha_y$, and the acceleration $\alpha_z$ at a predetermined sampling frequency, and inputs data indicating the detected accelerations to the speed calculation section 138 and the attitude angle calculation section 140.

(Speed Calculation Section 138)

The speed calculation section 138 divides the acceleration rate $\alpha_z$ along the Z-axis input from the 3-axis acceleration sensor 118 by the pitch rate $\omega_y$ input from the Y-axis gyro sensor 116, thereby calculating a speed V in the travelling direction, and inputs the calculated speed V to the position calculation section 136.

(Position Calculation Section 136)

The position calculation section 136 has a function of calculating position information of a current position based on the speed V calculated by the speed calculation section 138 and the angle θ calculated by the angle calculation section 134. Specifically, the position calculation section 136 calculates an amount of change from the position at the previous calculation to the current position based on the speed V and the angle θ. Then, the position calculation section 136 supplies the control section 150 with the amount of change.

(Attitude Angle Detection Section 140)

The attitude angle calculation section 140 generates, to begin with, attitude angle data indicating an attitude angle of the PND 10 by performing a predetermined attitude angle detection processing based on the acceleration rate data $\alpha_x$, $\alpha_y$, and $\alpha_z$ which are input from the 3-axis acceleration sensor 118, and inputs the attitude angle data to the azimuth calculation section 142.

(Geomagnetic Sensor 120)

The geomagnetic sensor 120 is a sensor having a function of detecting, as voltage values, geomagnetism $M_x$, geomagnetism $M_y$, and geomagnetism $M_z$ in the X-axis direction, the Y-axis direction, and the Z-axis direction, respectively. The geomagnetic sensor 120 inputs the detected geomagnetism data $M_x$, $M_y$, and $M_z$ to the azimuth calculation section 142.

(Azimuth Calculation Section 142)

The azimuth calculation section 142 performs a predetermined correction processing to the geomagnetism data $M_x$, $M_y$, and $M_z$ input from the geomagnetic sensor 120, and generates azimuth data indicating an azimuth of the PND 10 based on the corrected geomagnetism data and the attitude angle data input from the attitude angle detection section 140. The azimuth calculation section 142 supplies the navigation section 150 with the generated azimuth data.

That is, the geomagnetic sensor 120, the 3-axis acceleration sensor 118, the attitude angle calculation section 140, and the azimuth calculation section 142 each function as a so-called electronic compass and generates the azimuth data. Mainly in the case where the PND 10 is used by being detached from the cradle 14 (for example, in the case where the PND 10 is used when the user is walking), the control section 150 uses the azimuth data and provides the user with map data which is being displayed in a manner that the direction of the map data is adjusted to the direction of the PND 10. Note that, when the PND 10 is operated in an in-car mode, the PND 10 may associate driving history with a road in the map data, and may provide the user with the map data, the direction of which is adjusted to the direction of the PND 10 based on the azimuth of the map. Alternatively, the PND 10 can provide the user with map data, the direction of which is adjusted to the direction obtained by calculating the direction of the PND 10 using an acquired GPS azimuth.

(Pressure Sensor 122)

The pressure sensor 122 is a sensor having a function of detecting, as a voltage value, the surrounding pressure. The pressure sensor 122 detects a pressure at a predetermined sampling frequency, and inputs the detected pressure data to the altitude calculation section 144.

(Altitude Calculation Section 144)

The altitude calculation section 144 calculates the altitude of the PND 10 based on the pressure data input from the pressure sensor 122, and provides the control section 150 with the calculated altitude data.

(Control Section 150)

The control section 150 has a function of controlling entire operation of the PND 10. For example, as shown in FIG. 4, the control section 150 mainly has functions of an altitude information acquisition section 151, an altitude increase rate calculation section 153, a position information acquisition section 155, a navigation section 157, a degree-of-risk determination section 159, and an output control section 161.

(Altitude Information Acquisition Section 151)

The altitude information acquisition section 151 has a function of acquiring an altitude of a current point. The altitude information acquisition section 151 can acquire altitude data calculated by the altitude calculation section 144 as the altitude of the current point, for example. Alternatively, the altitude information acquisition section 151 may also acquire altitude data that can be acquired based on GPS signals as the altitude of the current point. The altitude information acquisition section 151 can supply the altitude increase rate calculation section 153 and the degree-of-risk determination section 159 with the acquired altitude of the current point. Note that the altitude information acquisition section 151 may record the acquired altitude of the current point in the storage section 102, and thereby generating altitude history information.

(Altitude Increase Rate Calculation Section 153)

The altitude increase rate calculation section 153 is an example of a calculation section, and has a function of calculating a rate of increase in altitude based on altitude information. The rate of increase in altitude calculated by the altitude increase rate calculation section 153 may be a rate of increase in altitude based on actual travel history up to a current time point. Alternatively, the rate of increase in altitude calculated by the altitude increase rate calculation section 153 may be a rate of increase in altitude which is to be estimated thereafter. The estimated rate of increase in altitude can be calculated using information of a planned route to be taken thereafter that is supplied from the navigation section 157, for example. The altitude increase rate calculation section 153 may estimate future travel speed using actual travel speed up to a current time point, and may calculate the estimated rate of increase in altitude in the case of travelling the planned route to be taken thereafter at the estimated travel speed. In this case, the altitude increase rate calculation section 153 can also calculate the estimated rate of increase in altitude using corrected estimated travel speed for the actual travel speed up to the current time point in accordance with the altitude difference of the planned route. For example, in the case where the altitude difference of the planned route is large, the altitude increase rate calculation section 153 can perform correction such that the estimated travel speed becomes small. Even in the case of travelling the same distance, it is considered that a larger altitude difference decreases the travel speed. Accordingly, the estimated travel speed that is corrected in accordance with the altitude difference is used, and thus, more accurate travel time can be calculated. Therefore, further accurate estimated rate of increase in altitude is calculated.

Further, the altitude increase rate calculation section 153 can divide a route into multiple intervals, and can calculate the rate of increase in altitude for each of the divided intervals.

The dividing up of the route may be performed simply for each predetermined distance, for example. Alternatively, the dividing up of the route may be performed based on an altitude of the route. In this case, the altitude increase rate calculation section 153 can divide the route into multiple intervals based on the degree of altitude change, for example.

(Position Information Acquisition Section 155)

The position information acquisition section 155 has a function of acquiring position information of a current point of the PND 10. The position information acquisition section 155 can acquire information of an absolute position supplied from the GPS processing section 132, for example. Further, the position information acquisition section 155 can acquire the amount of change from the position at the previous calculation to the current position supplied from the position calculation section 136, and can also calculate position information using autonomous navigation. Further, the position information acquisition section 155 can also acquire the azimuth of the PND 10 supplied from the azimuth calculation section 142. Further, the position information acquisition section 155 can also acquire the altitude data of the PND 10 supplied from the altitude calculation section 144. The position information acquisition section 155 can acquire the current position information of the PND 10, by selecting information from the acquired various pieces of information or by combining the acquired various pieces of information.

Further, when the PND 10 is being operated in an in-car mode, the position information acquisition section 155 may identify the road on which a user is travelling using map matching processing based on the acquired current position information and road network data included in map data, and may perform correction such that the position information represents a position on a road. Further, the position information acquisition section 155 may acquire more accurate position information by executing any other position information correction processing.

(Navigation Section 157)

The navigation section 157 has a function of showing a course according to the selected route. The navigation section 157 causes the output control section 161 to display various types of display screen, and thus can show the course to the user, for example. For example, the navigation section 157 can show the course by causing an arrow to be displayed on the map, which indicates the direction in which the user turns, just before the user arrives at the intersection at which the user is to turn. Further, the output control section 161 controls the audio output section 106, causes the audio output section 106 to output audio, and thus, the navigation section 157 can also show the course to the user.

Further, the navigation section 157 also has a function of a route search section which searches for a route to be shown. For example, the navigation section 157 has a function of searching for a route from a current point to a specified destination. Note that the navigation section 157 may search for a suitable route depending on an operation mode of the PND 10. The operation mode may include, for example, an in-car mode, a pedestrian mode, and a bicycle mode. For example, the operation mode may be switched in accordance with user operation, or may be configured such that the operation mode is automatically switched to the pedestrian mode when detecting the detachment from the cradle 14. For example, while the PND 10 is operating in the in-car mode, the navigation section 157 can search for a route including an expressway. Further, while the PND 10 is operating in the in-car mode, the navigation section 157 can also search for a route that avoids a section in which a traffic jam is expected, using traffic jam prediction. Alternatively, while the PND 10 is operating in the pedestrian mode, the navigation section 157 can search for a route suitable for walking, such as an underground passage, a station concourse, a pedestrian bridge, and a park, using pedestrian map data that is different from the in-car map data. Further, while the PND 10 is operating in the bicycle mode, the navigation section 157 can set a route suitable for travelling by a bicycle. For example, while the PND 10 is operating in the bicycle mode, since the navigation section 157 searches narrow roads along which it is difficult for a car to pass, the navigation section 157 can search for a road more suitable for the bicycle. When the altitude increase rate calculation section 153 calculates the predicted rate of increase in altitude of the future, the navigation section 157 can supply the altitude increase rate calculation section 153 with information of the planned route. That is, the navigation section 157 may be an example of a planned route acquisition section.

(Degree-of-Risk Determination Section 159)

The degree-of-risk determination section 159 is an example of a determination section which determines a degree of risk of physical strain on the user based on altitude information. The degree-of-risk determination section 159 can determine the degree of risk based on a current altitude. As described above, the symptoms of altitude sickness are particularly likely to appear when the altitude is 2400 meters or more. Accordingly, when the current altitude is 2400 meters or more, the degree-of-risk determination section 159 can determine that the degree of risk is high. Further, even in the case where the altitude is 2000 meters or more, when the altitude rises rapidly, the symptoms of altitude sickness are likely to appear. Accordingly, even when the altitude is below 2400 meters, when it is 2000 meters or more, the degree-of-risk determination section 159 can determine the degree of risk based on the rate of increase in altitude calculated by the altitude increase rate calculation section 153. Note that 2000 meters is an example of a first threshold of the altitude. Further, 2400 meters is an example of a second threshold which is larger than the first threshold. The degree-of-risk determination section 159 may determine the degree of risk based on the rate of increase in altitude based on actual travel history information. Alternatively, the degree-of-risk determination section 159 may determine the degree of risk further based on the estimated rate of increase in altitude. In this case, in the case where the estimated rate of increase in altitude is calculated for each of multiple divided intervals, the degree-of-risk determination section 159 can determine the degree of risk based on the rate of increase in altitude of each interval. The degree-of-risk determination section 159 can perform the determination of the degree of risk based on the rate of increase in altitude using a threshold. The threshold used here may be a predetermined value, or may be selected by a user. Alternatively, the threshold used here may be a value adjusted by learning.

(Output Control Section 161)

The output control section 161 controls output of warning information that is output when the degree of risk is determined to be high by the degree-of-risk determination section 159. The output control section 161 can control the output of the warning information by controlling display of the display section 12, for example. Further, the output control section 161 can control the output of the warning information by controlling the audio output section 106. Here, it is preferred that the warning information include, in addition to the fact that the degree of risk is high, the reason that the degree of risk is determined to be high. For example, in the case where it is determined that the altitude of the current point is 2000 meters or higher and that the rate of increase in altitude is high, the output control section 161 can control the output of warning information that warns of a danger caused by rapid altitude rise. Further, in the case where the altitude of the current point is 2400 meters or higher, the output control section 161 can control the output of the warning information that warns of a danger caused by high altitude.

Heretofore, there have been shown some of the examples of the functions of the PND 10 according to the present embodiment. Each of the above structural elements may be configured using general-purpose members or circuits, or may be configured using hardware specialized for the function of each structural element. Further, the function of each structural element may be realized by reading out, by an arithmetic unit such as a CPU (Central Processing Unit), a control program from the storage medium such as a ROM (Read Only Memory) or a RAM (Random Access Memory) that stores the control program in which procedures for realizing those functions are written, and by interpreting and executing the program. Therefore, the configuration to be used can be changed appropriately in accordance with the technical level each time when the embodiment is carried out.

Note that there may be produced a computer program for realizing each function of the PND 10 according to the present embodiment as described above, and the computer program can be implemented in a personal computer or the like. Further, there can also be provided a computer-readable recording medium having the computer program stored therein. Examples of the recording medium include a magnetic disk, an optical disc, a magneto-optical disk, and a flash memory. Further, the computer program may be distributed via a network, without using the recording medium, for example.

[2-2. Operation Example]

Figure 5:
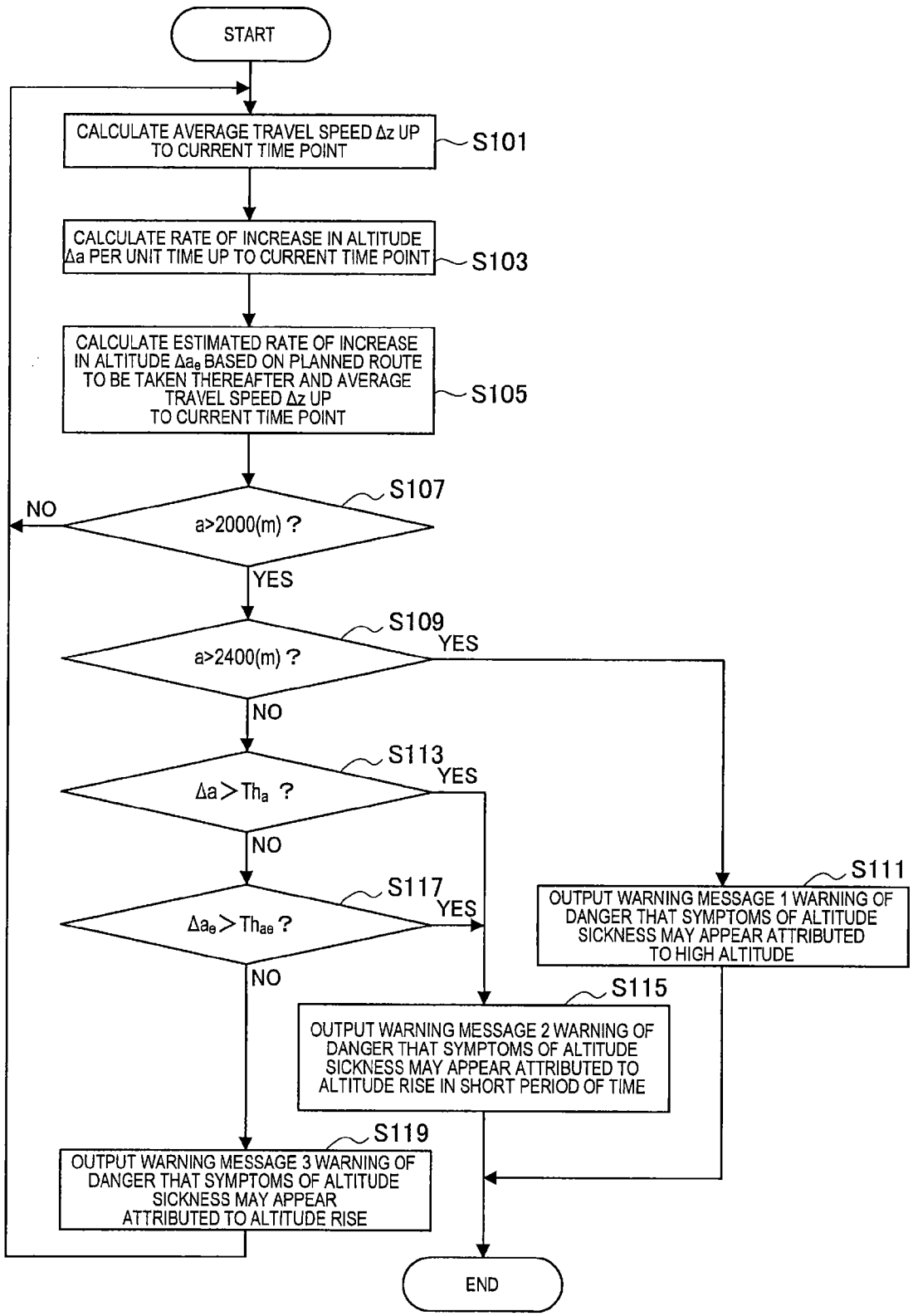
FIG. 5 is a flowchart showing operation of the PND according to the embodiment.
Figure 6:
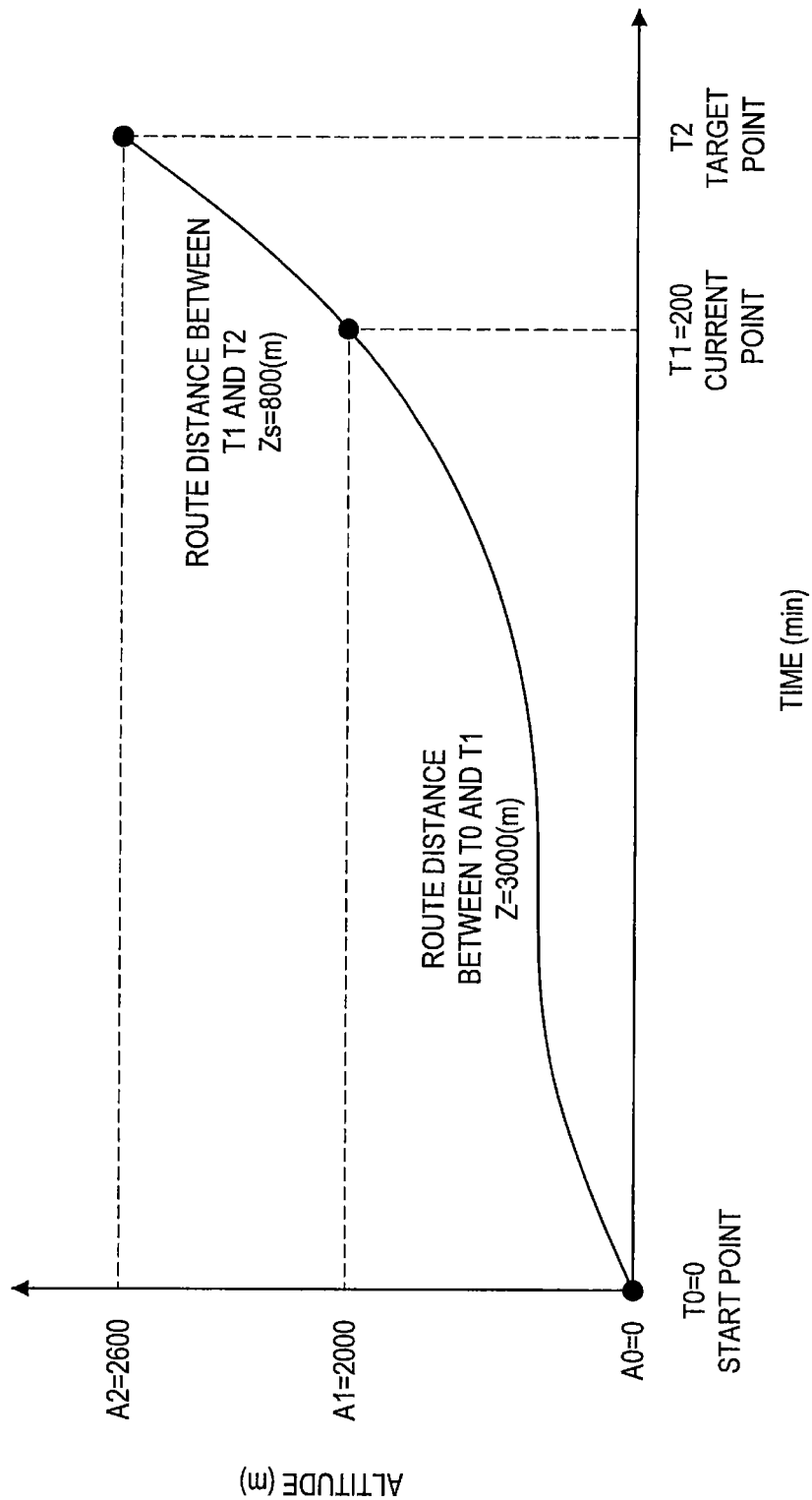
FIG. 6 is a graph showing a relationship between time and altitude as a user illustrated in the embodiment travels from a start point to a target point.
Figure 8:
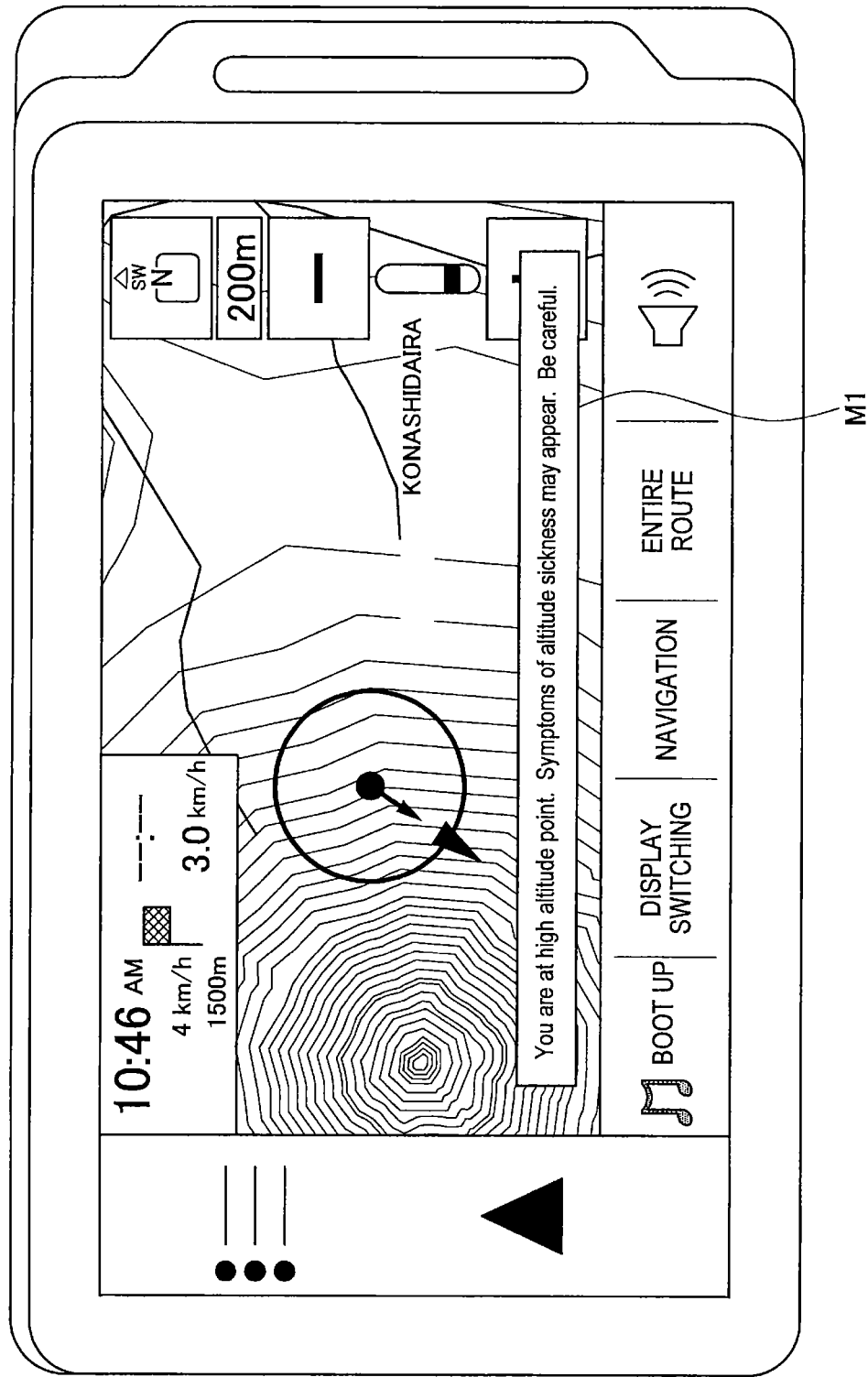
FIG. 8 is an explanatory diagram showing an example of a warning message-display screen of the PND according to the embodiment.

Next, with reference to FIGS. 5 to 8, there will be described an example of operation related to calculation of degree of risk and warning performed by the PND 10 according to the embodiment. FIG. 5 is a flowchart showing operation of the PND according to the embodiment. FIG. 6 is a graph showing a relationship between time and altitude as a user illustrated in the embodiment travels from a start point to a target point. FIG. 7 is a table showing an example of warning messages output by the PND according to the embodiment. FIG. 8 is an explanatory diagram showing an example of a warning message-display screen of the PND according to the embodiment.

First, referring to FIG. 5, the altitude increase rate calculation section 153 calculates average travel speed $\Delta z$ up to a current time point (S101). The description will be made using the example of FIG. 6. The average travel speed $\Delta z$ may be, where the present time point is represented by T1, the average travel speed from a start time point T0 to the present time point T1. The altitude increase rate calculation section 153 can calculate the average travel speed $\Delta z$ using the distance (Z=3000 m) and the travel time (T1−T0=200 min) up to the current time point, for example.

After that, the altitude increase rate calculation section 153 calculates the rate of increase in altitude $\Delta a$ per unit time up to the current time point (S103). Further, the altitude increase rate calculation section 153 calculates estimated rate of increase in altitude $A\alpha_e$ based on a planned route to be taken thereafter that is acquired by the navigation section 157 and the average travel speed $\Delta z$ up to the current time point (S105). Note that the estimated rate of increase in altitude $A\alpha_e$ is rate of increase in altitude which is estimated for the case of travelling along the route to be taken at the average travel speed $\Delta z$ up to the current time point. The average travel speed $\Delta z$ used here may be a value in which an altitude difference between two points is taken into consideration, or may be a value in which the altitude difference is not taken into consideration.

Next, the degree-of-risk determination section 159 determines whether an altitude a of the current point is higher than 2000 meters (S107). In the case where the altitude a of the current point is higher than 2000 meters, the degree of risk that symptoms of altitude sickness may appear rises. Accordingly, next, the degree-of-risk determination section 159 determines whether the altitude a of the current point is higher than 2400 meters (S109). Here, in the case where it is determined that the altitude a of the current point is higher than 2400 meters, the degree of risk that symptoms of altitude sickness may appear further increases. Therefore, the degree-of-risk determination section 159 instructs the output control section 161 to output a warning message 1, and the output control section 161 controls the output of the warning message 1 (S111).

The warning message 1 is a message that warns of the danger that the symptoms of altitude sickness may appear attributed to high altitude, and as shown in FIG. 7, for example, the message may be as follows: "You are at high altitude point. Symptoms of altitude sickness may appear. Be careful." The warning message may be, as shown in FIG. 8, for example, provided to the user in a manner that a warning message M1 is displayed by being superimposed on a map display screen. Alternatively, the warning message may be provided to the user using audio output.

Referring back to FIG. 5 again, in the case where it is determined in Step S109 that the altitude a of the current point is 2400 meters or lower, the degree-of-risk determination section 159 then determines whether the rate of increase in altitude $\Delta a$ up to the current time point is larger than a predetermined threshold $Th_a$ (S113). Here, in the case where the rate of increase in altitude $\Delta a$ up to the current time point is larger than the predetermined threshold $Th_a$, the degree-of-risk determination section 159 instructs the output control section 161 to output a warning message 2, and the output control section 161 controls the output of the warning message 2 (S115).

The warning message 2 is a message that warns of the danger that the symptoms of altitude sickness may appear attributed to altitude rise in a short period of time, and as shown in FIG. 7, for example, the message may be as follows: "Rapid altitude rise. Symptoms of altitude sickness may appear. Be careful." The method of outputting the warning message is the same as the case of outputting the warning message 1, and hence, the description is omitted here. Referring to the warning message, the user can take an action, for example, slowing down the movement pace or taking a break.

Referring back to FIG. 5 again, in the case where it is determined in Step S113 that the rate of increase in altitude $\Delta a$ up to the current time point is the predetermined threshold $Th_a$ or lower, the degree-of-risk determination section 159 then determines whether the estimated rate of increase in altitude $\Delta a_e$ is larger than a predetermined threshold $Th_{ae}$ (S117). Here, in the case where the estimated rate of increase in altitude $A\alpha_e$ is larger than the predetermined threshold $Th_{ae}$, the degree-of-risk determination section 159 instructs the output control section 161 to output the warning message 2, and the output control section 161 controls the output of the warning message 2 (S115).

On the other hand, in the case where it is determined in Step S117 that the estimated rate of increase in altitude $A\alpha_e$ is the predetermined threshold $Th_{ae}$ or less, the degree-of-risk determination section 159 instructs the output control section 161 to output a warning message 3, and the output control section 161 controls the output of the warning message 3 (S119).

The warning message 3 is a message that warns of the danger that the symptoms of altitude sickness may appear attributed to altitude rise, and as shown in FIG. 7, for example, the message may be as follows: "Altitude is high. Symptoms of altitude sickness may appear. You are recommended to take a break." The method of outputting the warning message is the same as the case of outputting the warning message 1, and hence, the description is omitted here.

[2-3. Calculation of Rate of Increase in Altitude]

Here, the calculation of rate of increase in altitude $\Delta a$ will be described in more detail using the example of FIG. 6. According to the example shown in FIG. 6, mountain climbing is started from a start time point T0, and the time (time T1) when 200 (min) is elapsed is set as a current time point. The altitude at that time is a=A1=2000 (m). Further, the route distance traveled from T0 to T1 is set to Z=3000 (m). Further, the route distance of the planned route up to a target point is Zs=800 (m).

In this case, the rate of increase in altitude $\Delta a$ up to the current time point is calculated by dividing the altitude difference between travel points by travel time. For example, in the example shown in FIG. 6, the altitude difference between the travel points is as follows.

$$A1-A0=2000-0=2000 \text{ (m)}$$

Further, the travel time is as follows.

$$T1-T0=200-0=200 \text{ (min)}$$

Therefore, the rate of increase in altitude $\Delta a$ is as follows.

$$\Delta a = 2000/200 = 10 \text{ (m/min)}$$

[2-4. Calculation of Average Travel Speed]

Here, continuously with reference to the example shown in FIG. 6, the calculation of average travel speed will be described. First, the altitude increase rate calculation section 153 calculates average travel speed $\Delta z$ from T0 to T1. The altitude increase rate calculation section 153 uses the average travel speed $\Delta z$ for calculating an estimated rate of increase in altitude $A\alpha_e$ from then on. Specifically, the altitude increase rate calculation section 153 calculates the estimated rate of increase in altitude $A\alpha_e$ in the case where a user continues travelling the planned route at the average travel speed up to the current time point. Therefore, first, the average travel speed $\Delta z$ is calculated.

The average travel speed $\Delta z$ may be a value taking into consideration the altitude difference between two points, or may be a value not taking into consideration the altitude difference.

For example, in the case where the altitude difference is not taken into consideration, the average travel speed $\Delta z$ is represented by the following formula.

$$\Delta z = \text{travel distance/travel time} = 3000/200 = 15 \text{ (m/min)}$$

Note that the travel distance may be an actual travel distance along a slope between two points, or may be a horizontal distance between two points on a map.

Further, the average travel speed $\Delta z$, in the case where the increase in altitude is taken into consideration is represented by the following formula.

$$\Delta z_a = \Delta z \times ((\text{travel distance} + \text{altitude difference})/\text{travel distance})$$
$$= 15 \times ((3000 + 2000)/3000) = 25 \text{(m/min)}$$

The estimated rate of increase in altitude is calculated using the average travel speed $\Delta z$ or the average travel speed $\Delta z_a$.

[2-5. Calculation of Estimated Rate of Increase in Altitude]

Next, continuously with reference to the example shown in FIG. 6, the calculation of estimated rate of increase in altitude will be described. The estimated rate of increase in altitude is, as described above, the rate of increase in altitude which is estimated for the case where the user continues travelling the planned route at the average travel speed up to the current time point. For the average travel speed there may be used the above-mentioned average travel speed $\Delta z$ or average travel speed $\Delta z_a$.

First, the estimated rate of increase in altitude $\Delta a_e$ obtained when the average travel speed $\Delta z$ not taking into consideration the altitude difference is used is represented by the following formula.

$$\Delta a_e = \frac{\text{planned route altitude difference}}{(\text{planned route distance/average travel speed})}$$
$$= (A2-A1)/(Zs/\Delta z)$$
$$= 600/(800/15) = 11.25 \text{(m/min)}$$

Next, the estimated rate of increase in altitude $\Delta a_{ea}$ obtained when the average travel speed $\Delta z_a$ taking into consideration the altitude difference is used is represented by the following formula.

$$\Delta a_{ea} = \Delta z_a/((\text{planned route distance} +$$
$$\text{planned route altitude differnce})/$$
$$\text{planned route distance})$$
$$= \Delta z_a/(((Zs+(A2-A1))/Zs)$$
$$= 25/(800+600/800) \approx 14.285$$

[2-6. Division into Intervals for Calculation]

Figure 9:
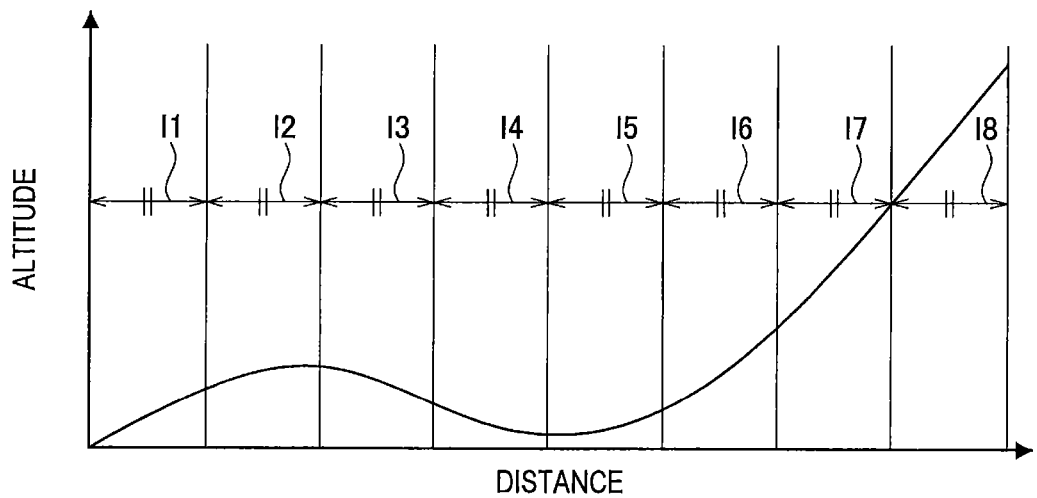
FIG. 9 is an explanatory diagram showing an example of division of a planned route into intervals executed by the PND according to the embodiment.
Figure 10:
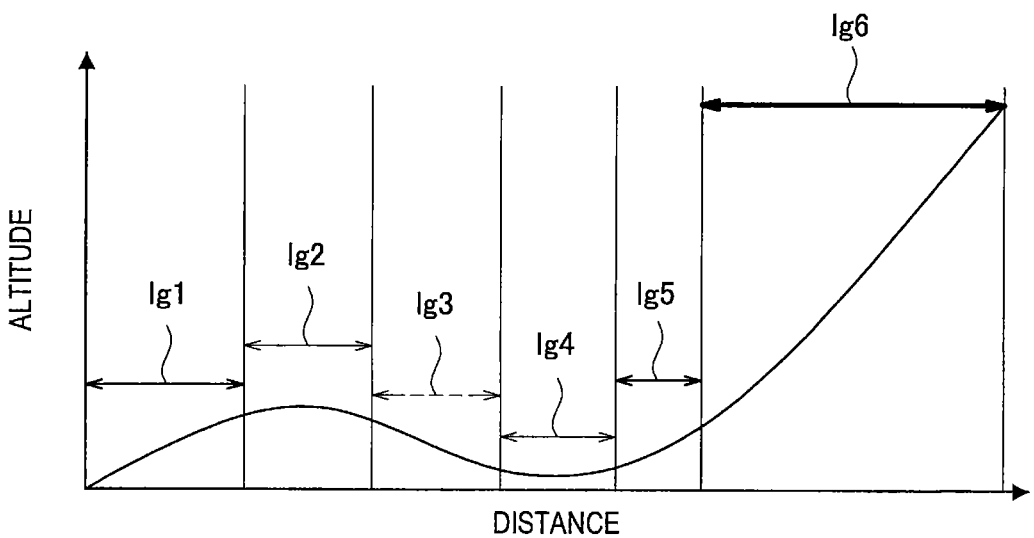
FIG. 10 is an explanatory diagram showing another example of division of the planned route into intervals executed by the PND according to the embodiment.

Next, there will be described division into calculation intervals of the rate of increase in altitude. In each of the examples described above, the degree of risk is determined by calculating the estimated rate of increase in altitude of the entire route from the current time point to the target point of the planned route. However, the present technology is not limited thereto, and the planned route may be divided into multiple intervals, and the rate of increase in altitude may be calculated for each of the divided intervals. The method of dividing into intervals will be described with reference to FIG. 9 and FIG. 10. FIG. 9 is an explanatory diagram showing an example of division of a planned route into intervals executed by the PND according to the embodiment. FIG. 10 is an explanatory diagram showing another example of division of the planned route into intervals executed by the PND according to the embodiment.

For example, as shown in FIG. 9, the altitude increase rate calculation section 153 may divide the planned route equally by a fixed distance into multiple intervals I1 to I8, and may calculate the estimated rate of increase in altitude for each of the intervals. The degree-of-risk determination section 159 uses the estimated rate of increase in altitude of each of the divided intervals, and thus can determine the degree of risk for each interval.

Further, for example, as shown in FIG. 10, the altitude increase rate calculation section 153 may divide the planned route by a fixed gradient group into multiple intervals Ig1 to Ig6 based on the gradient of the planned route, and may calculate the estimated rate of increase in altitude for each of the intervals. The degree-of-risk determination section 159 uses the estimated rate of increase in altitude of each of the divided intervals, and thus can determine the degree of risk for each interval.

3. Second Embodiment

Case of Determining Degree of Risk on Server Side

Next, a second embodiment of the present disclosure will be described. The second embodiment is an example in which a degree of risk is determined on a server side.

[3-1. Configuration]

Figure 11:
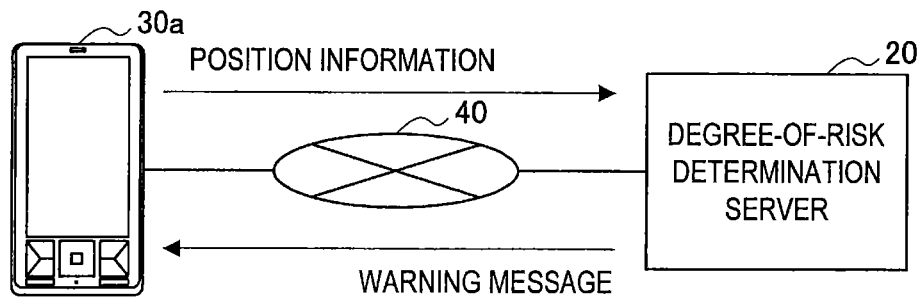
FIG. 11 is a configuration diagram of a degree-of-risk determination system according to a second embodiment of the present disclosure.
Figure 12:
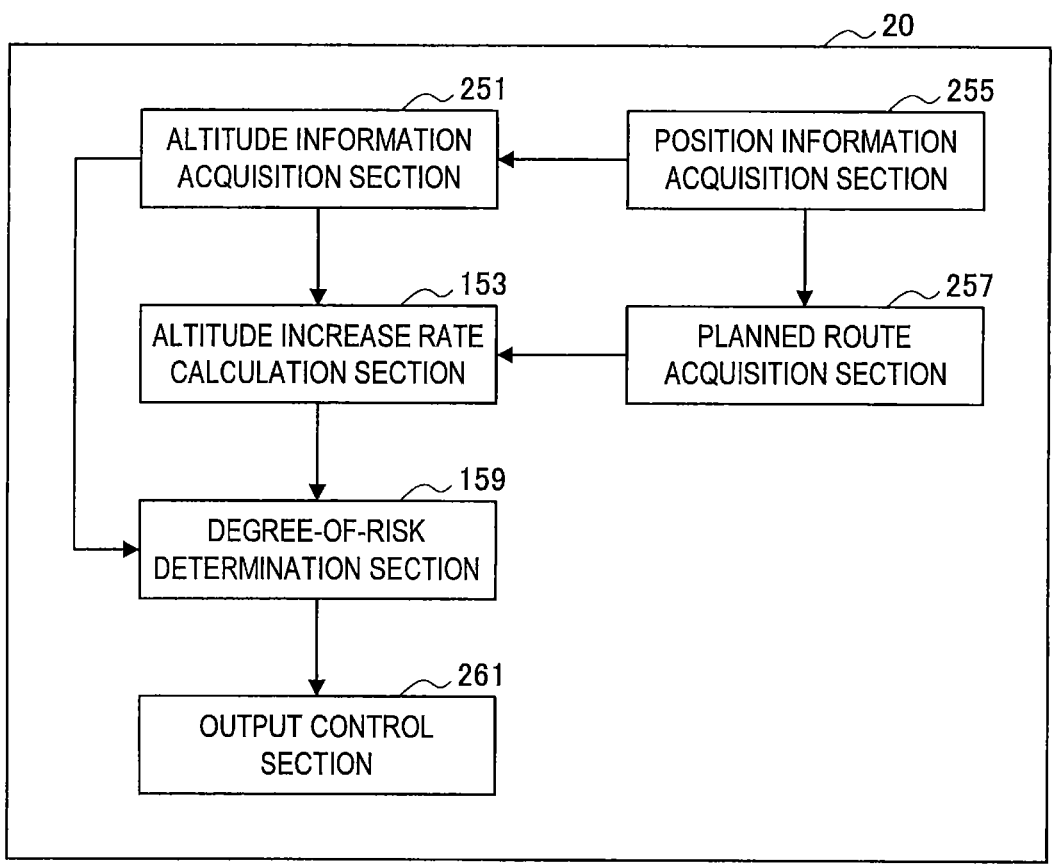
FIG. 12 is a block diagram showing a configuration of a degree-of-risk determination server according to the embodiment.
Figure 13:
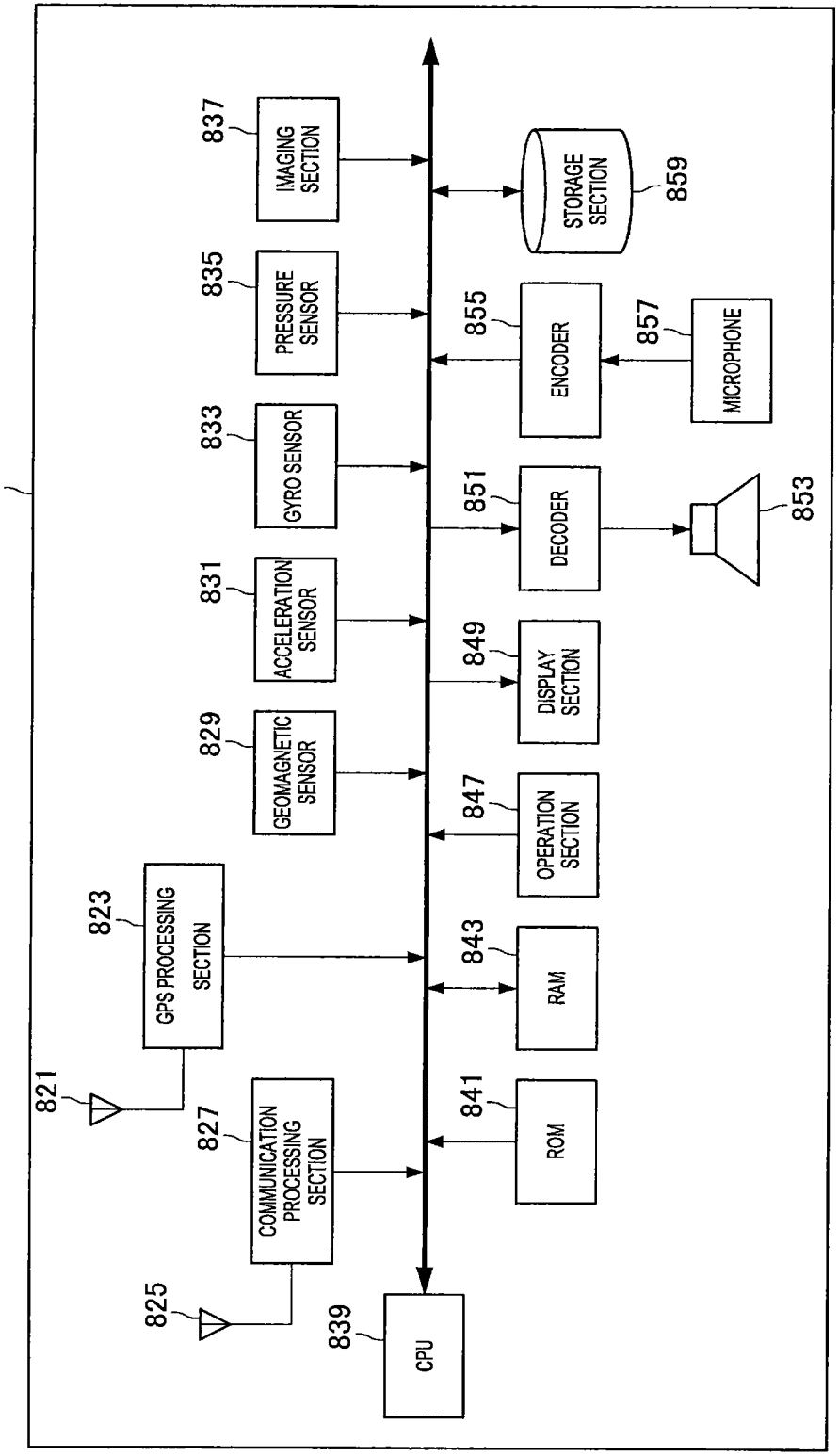
FIG. 13 is a block diagram showing a configuration of a mobile terminal according to the embodiment.

First, with reference to FIGS. 11 to 13, a configuration of a degree-of-risk determination system according to the embodiment will be described. FIG. 11 is the configuration diagram of the degree-of-risk determination system according to the second embodiment of the present disclosure. FIG. 12 is a block diagram showing a configuration of a degree-of-risk determination server according to the embodiment. FIG. 13 is a block diagram showing a configuration of a mobile terminal according to the embodiment.

Referring to FIG. 11, the degree-of-risk determination system according to the present embodiment includes a mobile terminal 30a and a degree-of-risk determination server 20 which are connected to each other via a network 40. The mobile terminal 30a may be an information processing apparatus such as a mobile phone, a mobile music playback device, a mobile video processing device, and a mobile game console, for example. The mobile terminal 30a transmits at least position information to the degree-of-risk determination server 20, and the degree-of-risk determination server 20 determines the degree of risk that the user of the mobile terminal 30a may suffer from altitude sickness based on the information received from the mobile terminal 30a. Then, when the degree of risk that the user may suffer from altitude sickness is high, the degree-of-risk determination server 20a outputs a warning message to the mobile terminal 30a.

((Degree-of-Risk Determination Server 20))

Referring to FIG. 12, there is shown a configuration of the degree-of-risk determination server 20. The degree-of-risk determination server 20 mainly includes an altitude information acquisition section 251, an altitude increase rate calculation section 153, a position information acquisition section 255, a planned route acquisition section 257, a degree-of-risk determination section 159, and an output control section 261.

(Altitude Information Acquisition Section 251)

The altitude information acquisition section 251 has a function of acquiring altitude information of a location at which the mobile terminal 30a is positioned. The altitude information acquisition section 251 can acquire the altitude information based on the position information acquired by the position information acquisition section 255 from the mobile terminal 30a, for example. In this case, the altitude information acquisition section 251 uses pieces of information of altitude at respective points included in map information, and thus can acquire the altitude information based on the position information, for example. Alternatively, in the case where the mobile terminal 30a has a function of acquiring the altitude information, the altitude information acquisition section 251 may receive the altitude information transmitted from the mobile terminal 30a, and thus may acquire the altitude information. The altitude information acquisition section 251 can supply the altitude increase rate calculation section 153 and the degree-of-risk determination section 159 with the altitude information.

(Position Information Acquisition Section 255)

The position information acquisition section 255 has a function of acquiring the position information of the mobile terminal 30a. The position information acquisition section 255 can supply the altitude information acquisition section 251 and the planned route acquisition section 257 with the acquired position information.

(Planned Route Acquisition Section 257)

The planned route acquisition section 257 has a function of acquiring information of a planned route that is planned by the user of the mobile terminal 30a. The planned route acquisition section 257 receives the information of the planned route from the mobile terminal 30a, and thus can acquire the information of the planned route, for example.

(Output Control Section 261)

The output control section 261 can control output of warning information based on the instruction issued by the degree-of-risk determination section 159. The output control section 261 can transmit a warning message to the mobile terminal 30a based on the instruction issued by the degree-of-risk determination section 159.

((Mobile Terminal 30))

Hereinafter, there will be described an example of a configuration of the mobile terminal 30. Referring to FIG. 13, the mobile terminal 30 includes, for example, a GPS antenna 821, a GPS processing section 823, a communication antenna 825, a communication processing section 827, a geomagnetic sensor 829, an acceleration sensor 831, a gyro sensor 833, a pressure sensor 835, an imaging section 837, a CPU (Central Processing Unit) 839, a ROM (Read Only Memory) 841, a RAM (Random Access Memory) 843, an operation section 847, a display section 849, a decoder 851, a speaker 853, an encoder 855, a microphone 857, and a storage section 859.

(GPS Antenna 821)

The GPS antenna 821 is an example of an antenna which receives a signal from a positioning satellite. The GPS antenna 821 is capable of receiving GPS signals from multiple GPS satellites, and inputs the received GPS signals to the GPS processing section 823.

(GPS Processing Section 823)

The GPS processing section 823 is an example of a calculation section which calculates position information based on the signals received from the positioning satellites. The GPS processing section 823 calculates current position information based on the multiple GPS signals input from the GPS antenna 821, and outputs the calculated position information. To be specific, the GPS processing section 823 calculates positions of the respective GPS satellites based on the orbital data of the GPS satellites, and calculates distances from the respective GPS satellites to the mobile terminal 30 based on the differences between transmission time and reception time of the GPS signals. Then, based on the calculated positions of the respective GPS satellites and the calculated distances from the respective GPS satellites to the mobile terminal 30, a current three-dimensional position can be calculated. Note that the orbital data of GPS satellites used here may be included in the GPS signals, for example. Alternatively, the orbital data of GPS satellites may be acquired from an external server via the communication antenna 825.

(Communication Antenna 825)

The communication antenna 825 is an antenna having a function of receiving a communication signal via a mobile communication network or a wireless LAN (Local Area Network) communication network, for example. The communication antenna 825 can supply the communication processing section 827 with a received signal.

(Communication Processing Section 827)

The communication processing section 827 has a function of performing various types of signal processing to the signal supplied by the communication antenna 825. The communication processing section 827 can supply the CPU 839 with a digital signal generated from the supplied analog signal.

(Geomagnetic Sensor 829)

The geomagnetic sensor 829 is a sensor for detecting geomagnetism as a voltage value. The geomagnetic sensor 829 may be a 3-axis geomagnetic sensor which detects geomagnetism in the X-axis direction, the Y-axis direction, and the Z-axis direction. The geomagnetic sensor 829 can supply the CPU 839 with the detected geomagnetic data.

(Acceleration Sensor 831)

The acceleration sensor 831 is a sensor for detecting acceleration as a voltage value. The acceleration sensor 831 may be a 3-axis acceleration sensor which detects acceleration along the X-axis direction, acceleration along the Y-axis direction, and acceleration along the Z-axis direction. The acceleration sensor 831 can supply the CPU 839 with the detected acceleration data.

(Gyro Sensor 833)

The gyro sensor 833 is a measuring instrument for detecting an angle or an angular velocity of an object. The gyro sensor 833 may be a 3-axis gyro sensor which detects a variable velocity (angular velocity) of the rotation angle around each of the X-axis, the Y-axis, and the Z-axis as a voltage value. The gyro sensor 833 can supply the CPU 839 with the detected angular velocity data.

(Pressure Sensor 835)

The pressure sensor 835 is a sensor for detecting the surrounding pressure as a voltage value. The pressure sensor 835 detects a pressure at a predetermined sampling frequency, and can supply the CPU 839 with the detected pressure data.

(Imaging Section 837)

The imaging section 837 has a function of capturing a still image or a moving image via a lens in accordance with control of the CPU 839. The imaging section 837 may cause the storage section 859 to store the captured image.

(CPU 839)

The CPU 839 functions as an arithmetic processing unit and a control unit, and controls the overall operation inside the mobile terminal 30 in accordance with various programs. Further, the CPU 839 may be a microprocessor. The CPU 839 can realize various functions in accordance with various programs.

(ROM 841, RAM 843)

The ROM 841 can store programs and arithmetic parameters used by the CPU 839. The RAM 843 temporarily stores programs used during execution of the CPU 839 and parameters that appropriately change during the execution thereof (Operation Section 847)

The operation section 839 has a function of generating an input signal used by a user for performing a desired operation. For example, the operation section 847 may be configured from, for example, an input section for inputting information by the user, such as a touch sensor, a mouse, a keyboard, a button, a microphone, a switch, and a lever, and an input control circuit which generates an input signal based on the input by the user and outputs the generated input signal to the CPU 839.

(Display Section 849)

The display section 849 is an example of an output device, and may be a liquid crystal display (LCD) device, an organic EL (organic light emitting diode (OLED)) display device, or the like. The display section 849 displays a screen to the user, and thereby being able to provide information.

(Decoder 851, Speaker 853)

The decoder 851 has a function of performing decoding, analog conversion, and the like of input data in accordance with the control of the CPU 839. For example, the decoder 851 performs decoding, analog conversion, and the like of the audio data input via the communication antenna 825 and the communication processing section 827, and outputs an audio signal to the speaker 853. The speaker 853 can output the audio based on the audio signal supplied from the decoder 851.

(Encoder 855, Microphone 857)

The encoder 855 has a function of performing digital conversion, encoding, and the like of input data in accordance with the control of the CPU 839. The encoder 855 can perform digital conversion, encoding, and the like of the audio data input from the microphone 857, and can output the audio data. The microphone 857 can collect and output the audio as an audio signal.

(Storage Section 859)

The storage section 859 is a device for storing data, and can include a storage medium, a recording device for recording data in the storage medium, a reading device for reading out the data from the storage medium, and a deletion device for deleting the data recorded in the storage medium. Here, as the storage medium, there may be used a non-volatile memory such as a flash memory, an MRAM (Magnetoresistive Random Access Memory), a FeRAM (Ferroelectric Random Access Memory), a PRAM (Phase change Random Access Memory), and an EEPROM (Electronically Erasable and Programmable Read Only Memory), and a magnetic recording medium such as an HDD (Hard Disk Drive).

Heretofore, the examples of the degree-of-risk determination server 20 and the mobile terminal 30 according to the present embodiment have been shown. Each of the above structural elements may be configured using general-purpose members or circuits, or may be configured using hardware specialized for the function of each structural element. Further, the function of each structural element may be realized by reading out, by an arithmetic unit such as a CPU (Central Processing Unit), a control program from the storage medium such as a ROM (Read Only Memory) or a RAM (Random Access Memory) that stores the control program in which procedures for realizing those functions are written, and by interpreting and executing the program. Therefore, the configuration to be used can be changed appropriately in accordance with the technical level each time when the embodiment is carried out.

Note that there may be produced a computer program for realizing respective functions of the degree-of-risk determination server 20 and the mobile terminal 30 according to the present embodiment as described above, and the computer program can be implemented in a personal computer or the like. Further, there can also be provided a computer-readable recording medium having the computer program stored therein. Examples of the recording medium include a magnetic disk, an optical disc, a magneto-optical disk, and a flash memory. Further, the computer program may be distributed via a network, without using the recording medium, for example.

[3-2. Operation]

Figure 14:
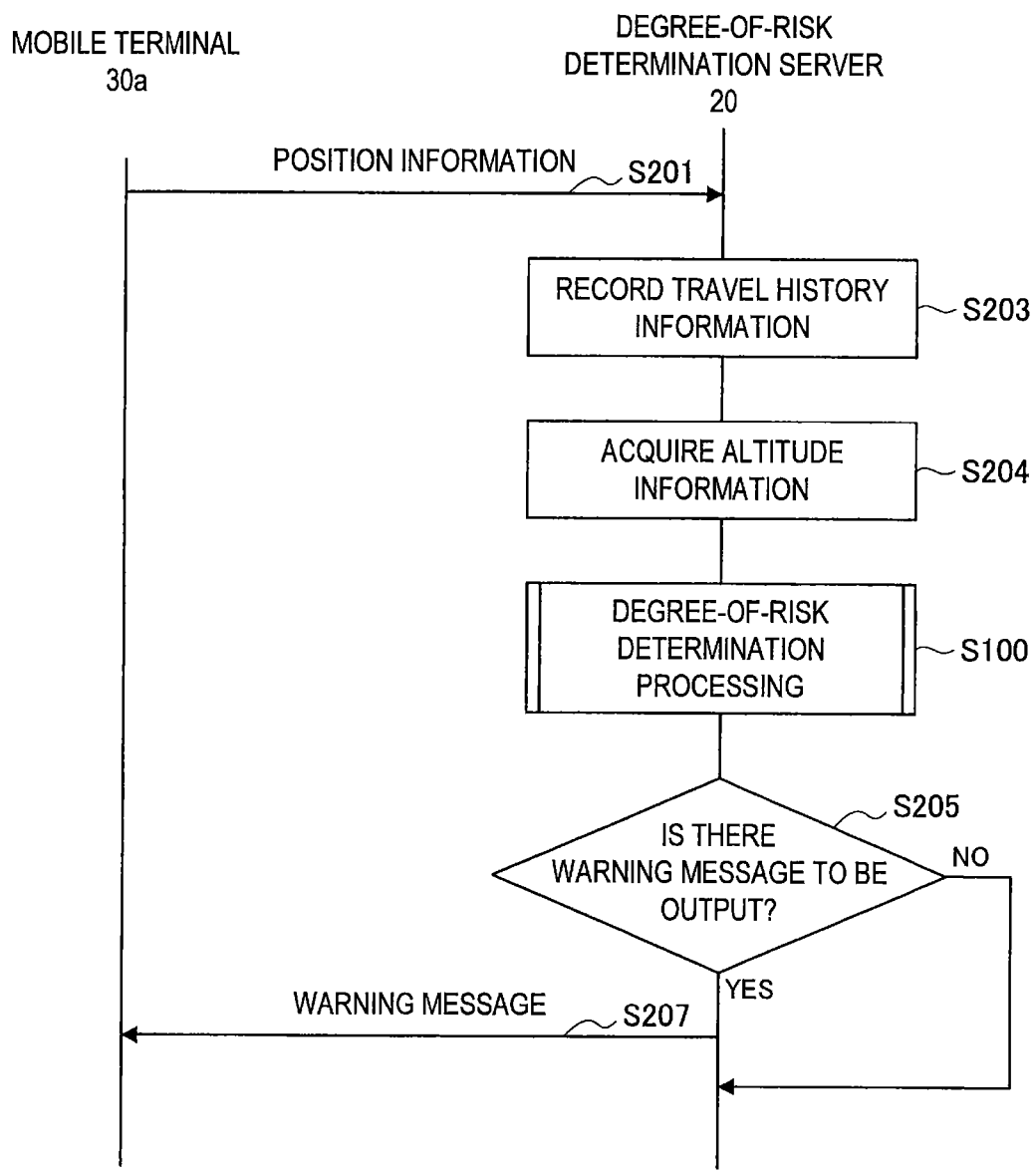
FIG. 14 is a sequence diagram showing operation of the degree-of-risk determination system according to the embodiment.

Next, with reference to FIG. 14, there will be described operation of the degree-of-risk determination system according to the embodiment. FIG. 14 is a sequence diagram showing operation of the degree-of-risk determination system according to the embodiment.

First, the mobile terminal 30a acquires position information and transmits the position information to the degree-of-risk determination server 20 (S201). In this case, the mobile terminal 30a may transmit position information of a current time point to the degree-of-risk determination server 20 each time. Further, the mobile terminal 30a may record the position information in association with date/time at which the position information is acquired, and may transmit, to the degree-of-risk determination server 20, the position information and the date/time corresponding to the position information.

Next, the degree-of-risk determination server 20 which has received the position information records the position information in association with the date/time at which the position information is acquired, and thus, generates travel history information (S203). Next, the degree-of-risk determination server 20 acquires altitude information (S204).

Then, the degree-of-risk determination server 20 executes the degree-of-risk determination processing (S100). Here, the degree-of-risk determination processing of Step S100 represents the processing of Steps S101 to S119 described in FIG. 5. Executing the degree-of-risk determination processing, the degree-of-risk determination server 20 determines whether there is a warning message to be output (S205). In the case where it is determined in Step S205 that there is a warning message to be output, the output control section 261 transmits the warning message to the mobile terminal 30 (S207).

4. Third Embodiment

Case of Notification System

Next, a third embodiment of the present disclosure will be described. The third embodiment is an example of a notification system which performs notification when the degree of risk that a user may suffer from altitude sickness is high.

[4-1. Configuration]

Figure 15:
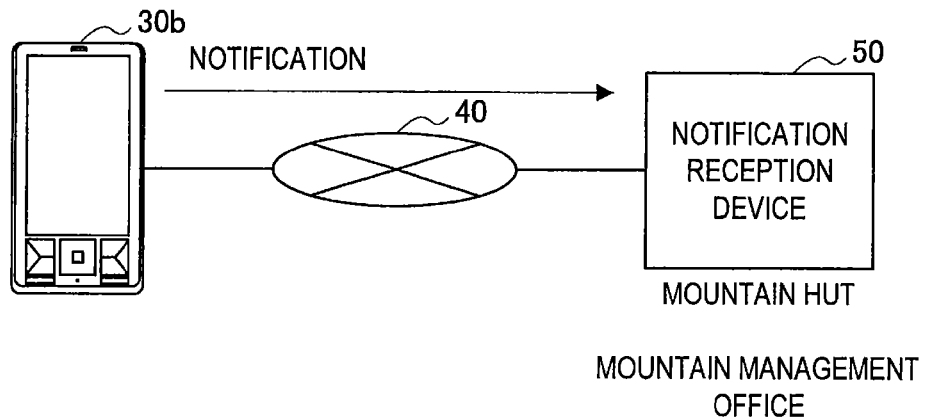
FIG. 15 is a configuration diagram of a degree-of-risk notification system according to a third embodiment of the present disclosure.
Figure 16:
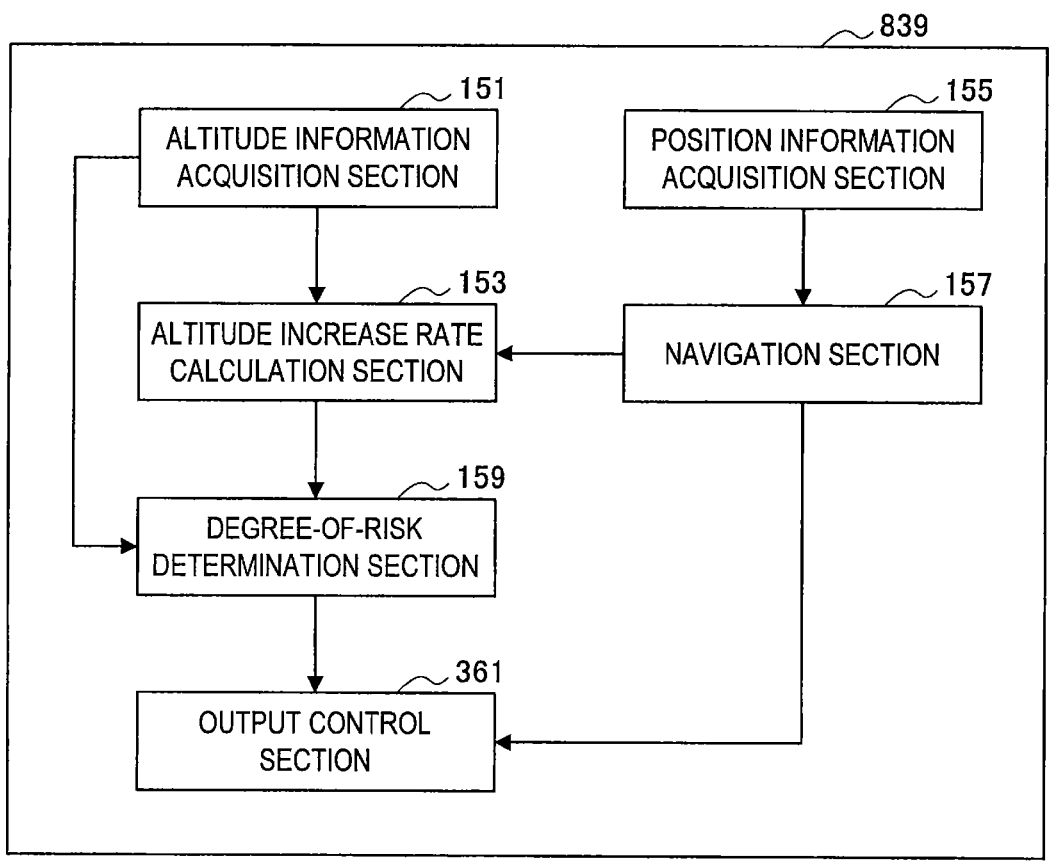
FIG. 16 is a block diagram showing a detailed configuration of a mobile terminal according to the embodiment.

First, with reference to FIG. 15 and FIG. 16, there will be described a configuration of the notification system according to the embodiment. FIG. 15 is a configuration diagram of a degree-of-risk notification system according to the third embodiment of the present disclosure. FIG. 16 is a block diagram showing a detailed configuration of a mobile terminal according to the embodiment.

Referring to FIG. 15, the notification system according to the present embodiment includes a mobile terminal 30b and a notification reception device 50 which is connected to the mobile terminal 30b via a network 40. The mobile terminal 30b may be an information processing apparatus such as a mobile phone, a mobile music playback device, a mobile video processing device, and a mobile game console, for example. The mobile terminal 30b determines the degree of risk that the user of the mobile terminal 30b may suffer from altitude sickness. Then, in the case where it is determined that the degree of risk is high, the mobile terminal 30b can notify the notification reception device 50 that the degree of risk is high. Here, the notification reception device 50 is an information processing apparatus having a communication function for receiving notification from the mobile terminal 30b. For example, the notification reception device 50 is desirably an information processing apparatus which is installed in a mountain hut, a mountain management office, or the like at the mountain that the user of the mobile terminal 30b is climbing, and which can be referred to by a person who can make a response for rescuing the user when receiving notification.

((Mobile Terminal 30b))

Referring to FIG. 16, there is shown a configuration of the mobile terminal 30b. Note that, the mobile terminal 30b has the entire configuration described in FIG. 13. Then, the functions shown in FIG. 16 are realized by operation of a CPU 839. Accordingly, the mobile terminal 30b mainly has functions of an altitude information acquisition section 151, an altitude increase rate calculation section 153, a position information acquisition section 155, a navigation section 157, a degree-of-risk determination section 159, and an output control section 361.

Note that the functions of the altitude information acquisition section 151, the altitude increase rate calculation section 153, the position information acquisition section 155, the navigation section 157, and the degree-of-risk determination section 159 are the same as the functions described in the first embodiment, and hence, the description thereof will be omitted.

(Output Control Section 361)

In addition to the function of the output control section 161, the output control section 361 has a function of performing notification to facilities such as a mountain but and a mountain management office nearby when the degree of risk that the user of the mobile terminal 30b may suffer from altitude sickness is high. The output control section 361 has a function of transmitting current position information of the mobile terminal 30b to the notification reception device 50, for example. The output control section 361 may also transmit, to the notification reception device 50, travel trajectory information during mountain climbing, a planned course to be taken thereafter, and information of the degree of risk that the user may suffer from altitude sickness, for example.

[4-2. Operation]

Figure 17:
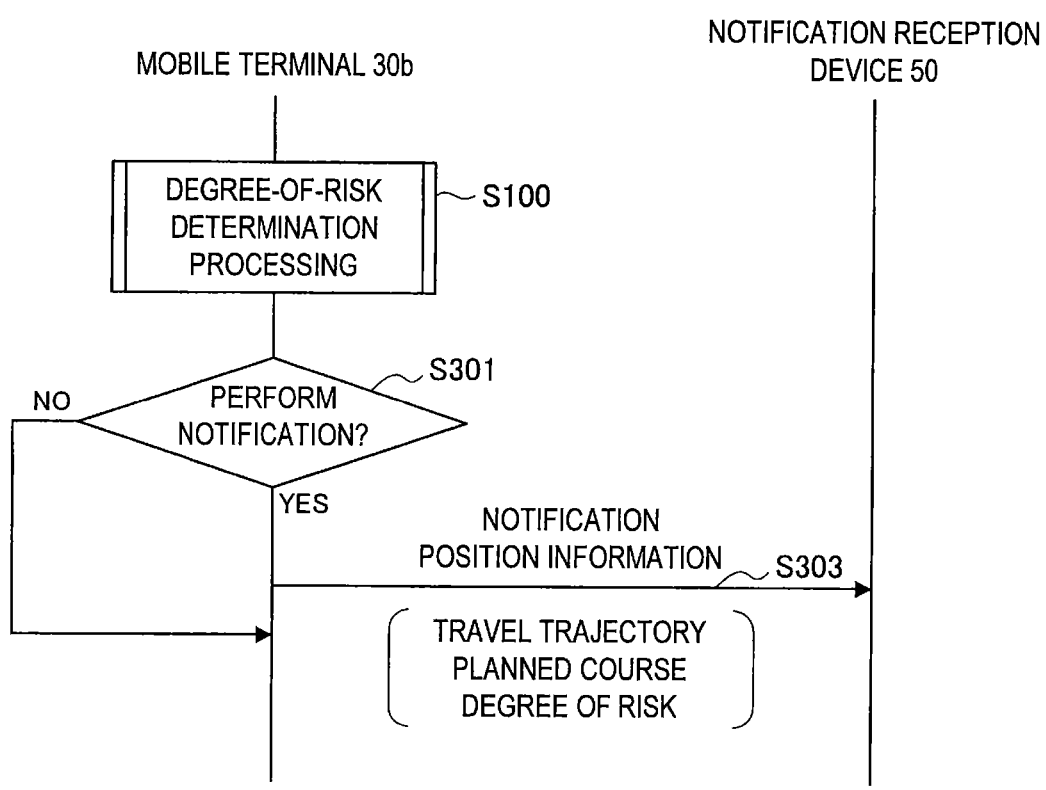
FIG. 17 is a sequence diagram showing operation of a degree-of-risk notification system according to the embodiment.

Next, with reference to FIG. 17, there will be described operation of the notification system according to the embodiment. FIG. 17 is a sequence diagram showing operation of a degree-of-risk notification system according to the embodiment.

First, the mobile terminal 30b executes the degree-of-risk determination processing (S100). The degree-of-risk determination processing represents the processing of Steps S101 to S119 described in FIG. 5. Executing the degree-of-risk determination processing, the output control section 361 of the mobile terminal 30b determines whether to perform notification (S301). Then, in the case of determining that the notification is to be performed, the output control section 361 performs notification including position information, for example (S303). The notification may include, as described above, travel trajectory information, a planned course, and information of a degree of risk.

It should be understood by those skilled in the art that various modifications, combinations, sub-combinations and alterations may occur depending on design requirements and other factors insofar as they are within the scope of the appended claims or the equivalents thereof.

For example, although the third embodiment shows an example of the notification system using a mobile phone, the present technology is not limited thereto. For example, in the case where a PND has communication functions, it may be configured such that the PND performs notification.

Note that in the present specification, the steps written in the flowchart or the sequence diagram may of course be processed in chronological order in accordance with the stated order, but may not necessarily be processed in the chronological order, and may be processed individually or in a parallel manner. It is needless to say that, in the case where the steps are processed in the chronological order, the order of the steps may be changed appropriately according to circumstances.

Additionally, the present technology may also be configured as below.

(1) An information processing apparatus including:
  an altitude information acquisition section which acquires altitude information; and
  a determination section which determines a degree of risk of physical strain on a user based on the altitude information.
(2) The information processing apparatus according to (1), further including
  a calculation section which calculates a rate of increase in altitude based on the altitude information,
  wherein the determination section determines the degree of risk based on the rate of increase in altitude.
(3) The information processing apparatus according to (2),
  wherein the calculation section calculates a rate of increase in altitude up to a current time point using a history of the altitude information.
(4) The information processing apparatus according to (2) or (3), further including
  a planned route acquisition section which acquires information of a planned route,
  wherein the calculation section calculates the rate of increase in altitude which is to be estimated thereafter, based on the information of the planned route, and
  wherein the determination section determines the degree of risk based on the rate of increase in altitude which is to be estimated thereafter.
(5) The information processing apparatus according to (4),
  wherein the calculation section calculates the rate of increase in altitude using an estimated travel speed corrected in accordance with an altitude difference of the planned route.
(6) The information processing apparatus according to (4) or (5),
  wherein the calculation section divides the planned route into a plurality of intervals, and calculates the rate of increase in altitude for each of the divided intervals, and
  wherein the determination section determines the degree of risk based on the rate of increase in altitude of each interval.
(7) The information processing apparatus according to (6),
  wherein the calculation section divides the planned route into a plurality of intervals based on an altitude of the planned route.
(8) The information processing apparatus according to (7),
  wherein the calculation section divides the planned route into a plurality of intervals based on a degree of altitude change of the planned route.
(9) The information processing apparatus according to any one of (1) to (8), further including
  an output control section which controls output of warning information when the degree of risk is determined to be high by the determination section.
(10) The information processing apparatus according to (9),
  wherein, when an altitude of a current point is determined to be a first threshold or more and the rate of increase in altitude is determined to be high, the output control section controls output of the warning information that warns of a danger caused by rapid altitude rise.
(11) The information processing apparatus according to (10),
  wherein, when an altitude of a current point is a second threshold or more, the second threshold being larger than the first threshold, the output control section controls output of the warning information that warns of a danger caused by high altitude.
(12) The information processing apparatus according to any one of (9) to (11),
  wherein the output control section controls output of a display screen including the warning information.
(13) The information processing apparatus according to any one of (9) to (12),
  wherein the output control section controls audio output of the warning information.
(14) The information processing apparatus according to any one of (9) to (13),
  wherein, when the degree of risk is determined to be high, the output control section controls output of notification information to a second information processing apparatus which is connected thereto via a communication path.
(15) The information processing apparatus according to (14), further including
  a position information acquisition section which acquires position information of current time,
  wherein the notification information includes at least the position information.
(16) The information processing apparatus according to (15),
  wherein the notification information further includes at least one of information of a planned travel route or the degree of risk.
(17) The information processing apparatus according to (5),
  wherein the calculation section divides the planned route into a plurality of intervals for each predetermined distance.
(18) An information processing method including:
  acquiring altitude information; and
  determining a degree of risk of physical strain on a user based on the altitude information.
(19) A program for causing a computer to function as an information processing apparatus including
  an altitude information acquisition section which acquires altitude information, and
  a determination section which determines a degree of risk of physical strain on a user based on the altitude information.
(20) A computer-readable recording medium having a program recorded therein, the program being for causing a computer to function as an information processing apparatus including
  an altitude information acquisition section which acquires altitude information, and
  a determination section which determines a degree of risk of physical strain on a user based on the altitude information.

The present disclosure contains subject matter related to that disclosed in Japanese Priority Patent Application JP 2011-175008 filed in the Japan Patent Office on Aug. 10, 2011, the entire content of which is hereby incorporated by reference.

What is claimed is:

1. An information processing apparatus comprising:
  an altitude information acquisition section which acquires altitude information;
  a determination section which determines a degree of risk of physical strain on a user based on the altitude information;
  a calculation section which calculates a rate of increase in altitude based on the altitude information,
  wherein the determination section determines the degree of risk based on the rate of increase in altitude; and
  a planned route acquisition section which acquires information of a planned route, wherein the calculation section calculates the rate of increase in altitude which is to be estimated thereafter, based on the information of the planned route, and wherein the determination section determines the degree of risk based on the rate of increase in altitude which is to be estimated thereafter.

2. The information processing apparatus according to claim 1, wherein the calculation section calculates the rate of increase in altitude up to a current time point using a history of the altitude information.

3. The information processing apparatus according to claim 1, wherein the calculation section calculates the rate of increase in altitude using an estimated travel speed corrected in accordance with an altitude difference of the planned route.

4. The information processing apparatus according to claim 1, wherein the calculation section divides the planned route into a plurality of intervals, and calculates the rate of increase in altitude for each of the divided intervals, and wherein the determination section determines the degree of risk based on the rate of increase in altitude of each interval.

5. The information processing apparatus according to claim 4, wherein the calculation section divides the planned route into a plurality of intervals based on an altitude of the planned route.

6. The information processing apparatus according to claim 5, wherein the calculation section divides the planned route into a plurality of intervals based on a degree of altitude change of the planned route.

7. The information processing apparatus according to claim 1, further comprising an output control section which controls output of warning information when the degree of risk is determined to be high by the determination section.

8. The information processing apparatus according to claim 7, wherein, when an altitude of a current point is determined to be a first threshold or more and the rate of increase in altitude is determined to be high, the output control section controls output of the warning information that warns of a danger caused by rapid altitude rise.

9. The information processing apparatus according to claim 8, wherein, when an altitude of a current point is a second threshold or more, the second threshold being larger than the first threshold, the output control section controls output of the warning information that warns of a danger caused by high altitude.

10. The information processing apparatus according to claim 7, wherein the output control section controls output of a display screen including the warning information.

11. The information processing apparatus according to claim 7, wherein the output control section controls audio output of the warning information.

12. The information processing apparatus according to claim 7, wherein, when the degree of risk is determined to be high, the output control section controls output of notification information to a second information processing apparatus which is connected thereto via a communication path.

13. The information processing apparatus according to claim 12, further comprising a position information acquisition section which acquires position information of current time, wherein the notification information includes at least the position information.

14. The information processing apparatus according to claim 13, wherein the notification information further includes at least one of information of a planned travel route or the degree of risk.

15. The information processing apparatus according to claim 3, wherein the calculation section divides the planned route into a plurality of intervals for each predetermined distance.

16. An information processing apparatus including:

an altitude information acquisition section which acquires altitude information;

a determination section which determines a degree of risk of physical strain on a user based on the altitude information;

a planned route acquisition section which acquires information of a planned route; and a calculation section which calculates a rate of increase in altitude which is to be estimated thereafter, based on the information of the planned route, wherein the determination section determines the degree of risk based on the rate of increase in altitude which is to be estimated thereafter.

17. A non-transitory computer-readable recording medium having a program recorded therein, the program being for causing a computer to function as an information processing apparatus including:

an altitude information acquisition section which acquires altitude information;

a determination section which determines a degree of risk of physical strain on a user based on the altitude information;

a planned route acquisition section which acquires information of a planned route; and a calculation section which calculates a rate of increase in altitude which is to be estimated thereafter, based on the information of the planned route, wherein the determination section determines the degree of risk based on the rate of increase in altitude which is to be estimated thereafter.

* * * * *